United States Patent [19]
Pescovitz

[11] Patent Number: 6,159,934
[45] Date of Patent: Dec. 12, 2000

[54] USE OF GHRH-RP TO STIMULATE STEM CELL FACTOR PRODUCTION

[75] Inventor: Ora H. Pescovitz, Carmel, Ind.

[73] Assignee: Indiana University Foundation, Bloomington, Ind.

[21] Appl. No.: 08/777,708

[22] Filed: Dec. 20, 1996

Related U.S. Application Data

[60] Provisional application No. 60/008,933, Dec. 20, 1995.
[51] Int. Cl.$^7$ .......................... C07K 14/575; C07K 14/60
[52] U.S. Cl. .............................. 514/12; 530/324; 930/120
[58] Field of Search ............................ 530/324; 930/120; 514/12

[56] References Cited

U.S. PATENT DOCUMENTS 5,017,557  5/1991  Fabbri et al. .............................. 514/12

OTHER PUBLICATIONS

K. Arase, T. Sakaguchi, M. Takahashi, G.A. Bray and N. Ling, "Effects On Feeding Behavior Of Rats Of A Cryptic Peptide From The C–Terminal End Of Prepro–Growth Hormone–Releasing Factor", *Endocrinology*, vol. 121, No. 6, pp. 1960–1965 (1987).

S.A. Berry and O.H. Pescovitz, "Identification Of A Rat GHRH–Like Substance And Its Messenger RNA In Rat Testis", *Endocrinology*, vol. 123, No. 1, pp. 661–663 (1988).

S.A. Berry and O.H. Pescovitz, "Ontogeny and Pituitary Regulation Of Testicular Growth Hormone–Releasing Hormone–Like Messenger Ribonucleic Acid", *Endocrinology*, vol. 127, No. 3, pp. 1404–1411 (1990).

B. Bloch, A. Baird, N. Ling and R. Guillemin, "Immunohistochemical Evidence That Growth Hormone–Releasing Factor (GRF) Neurons Contain An Amidated Peptide Derived From Cleavage Of The Carboxyl–Terminal End Of The GRF Precursor," *Endocrinology*, vol. 118, No. 1, pp. 156–162 (1986).

C.Y. Bowers, A.O. Sartor, G.A. Reynolds and T.M. Badger, "On The Actions Of The Growth Hormone–Releasing Hexapeptide, GHRP", *Endocrinology*, vol. 128, No. 4, pp. 2027–2035 (1991).

B.S. Monts, P.R. Breyer, J.K. Rothrock and O.H. Pescovitz, "Peptides Of The Growth Hormone–Releasing Hormone Family: Differential Expression In Rat Testis", *Endocrine*, vol. 4, No. 1, pp. 73–78 (Feb. 1996).

O.H. Pescovitz, S.A. Berry, M. Laudon, N. Ben–Jonathan, A. Martin–Myers, S.–M. Hsu, T.J. Lambros and A.M. Felix, "Localization And growth Hormone (GH)–Releasing Activity Of Rat Testicular GH–Releasing Hormone–Like Peptide", *Endocrinology*, vol. 127, No. 5, pp. 2336–2342 (1990).

O.H. Pescovitz, C.H. Srivastava, P.R. Breyer and B.A. Monts, "Paracrine Control Of Spermatogenesis", *TEM*, vol. 5, No. 3, pp. 126–131 (1994).

P. Rossi, S. Dolci, C. Albanesi, P. Grimaldi, R. Ricca and R. Geremia, "Follicle–Stimulating Hormone Induction Of Steel Factor (SLF) m RNA In Mouse Sertoli Cells And Stimulation Of DNA Synthesis In Spermatogonia By Soluble SLF", *Developmental Biology*, vol. 153, pp. 68–74 (1993).

C.H. Srivastava, P.R. Breyer, J.K. Rothrock, M.J. Peredo an O.H. Pescovitz, "A New Target For Growth Hormone Releasing–Hormone Action In Rat: The Sertoli Cell", *Endocrinology*, vol. 133, No. 3, pp. 1478–1481 (1993).

C.H. Srivastava, M.W. Collard, J.K. Rothrock, M.J. Peredo, S.A. Berry and O.H. Pescovitz, "Germ Cell Localization Of A Testicular Growth Hormone–Releasing Hormone–Like Factor", *Endocrinology*, vol. 133, No. 1, pp. 83–89 (1993).

C.H. Srivastava, M.R. Kelley, B.S. Monts, T.M. Wilson, P.R. Breyer and O.H. Pescovitz, "Growth Hormone–Releasing Hromone Receptor mRNA Is Present In Rat Testis" (1994).

C.H. Srivastava, B.S. Monts, J.K. Rothrock, M.J. Peredo and O.H. Pescovitz, "Presence Of A Spermatogenic–Specific Promotor In The Rat Growth Hormone–Releasing Hormone Gene", *Endocrinology*, vol. 136, No. 4, pp. 1502–1508 (1995).

Mayo,K.E., Cerelli, G.M., Rosenfeld, M.G. and Evans, R.M., "Characterization of cDNA and Genomic Clones Endcoding the Precursor to Rat Hypothalamic Growth Hormone–Releasing Factor," *Nature*, vol. 314, No. 4, pp. 464–467 (Apr. 4, 1985).

P.R. Breyer et al., "A Novel Peptide From the Growth Hormone Releasing Ormone Gene Stimulates Sertoli Cell Activity", Endocrinology 137(5) :2159, 1996.

*Primary Examiner*—Lorraine Spector
*Attorney, Agent, or Firm*—Woodard, Emhardt, Naughton, Moriarty & McNett

[57] ABSTRACT

Described are novel uses of GHRH-RP polypeptides for specifically activating Sertoli cell expression of stem cell factor and promoting spermatogenesis and fertility, and for inhibiting GHRH-RP activity to decrease or eliminate spermatogenesis and fertility. Also described are pharmaceutical compositions for such uses, and transgenic animals lacking expression of or expressing introduced DNA encoding GHRH-RP polypeptides.

8 Claims, 18 Drawing Sheets

(2 of 18 Drawing Sheet(s) Filed in Color)

A. Testicular GHRH transcript

"TESTIS EXON 1"

```
  1  CTGCGGATGCCACGGAACATCGAGCCAAATCCCAGGAACACGCTCTGAACCCCAGGAGCT   60
                                  | EXON 2         *
 61  GCACACCACTCTATTAGGTCCCGCCCAGGAGTGAAGGATGCCACTCTGGGTGTTCTTTGT  120
                                              MetProLeuTrpValPhePheVa
                                                                   l
121  GCTCCTCACCCTCACCAGTGGCTCCCACTGCTCACTGCCCCCCTCACCTCCCTTCAGGGT  180
     lLeuLeuThrLeuThrSerGlySerHisCysSerLeuProProSerProProPheArgVa
     EXON 3
181  GCGGCGGCATGCAGACGCCATCTTCACCAGCAGCTACCGGAGAATCCTGGGCCAATTATA  240
     lArgArgHisAlaAspAlaIlePheThrSerSerTyrArgArgIleLeuGlyGlnLeuTy
                                        | EXON 4
241  TGCCCGCAAACTGCTGCACGAAATCATGAACAGGCAGCAAGGGGAGAGGAACCAGGAACA  300
     rAlaArgLysLeuLeuHisGluIleMetAsnArgGlnGlnGlyGluArgAsnGlnGluGl
301  AAGATCCAGGTTCAACCGCCATTTGGACAGAGTGTGGGCAGAGGACAAGCAGATGGCCCT  360
     nArgSerArgPheAsnArgHisLeuAspArgValTrpAlaGluAspLysGlnMetAlaLe
                      | EXON 6
361  GGAGAGCATCTTGCAGGGATTCCCAAGGATGAAGCTTTCAGCGGAGGCTTGAGCCCTCGG  420
     uGluSerIleLeuGlnGlyPheProArgMetLysLeuSerAlaGluAlaEnd
421  CCCCCAAACATAGCTGGACCCTGTTACTTCTACTTCAGTTCTGATCTTCTCCTTCCTCTG  480
481  TGAATACAATAAAGACCCAGTTCTCATCTGCAAAAAAAAAAAAAAA               526
```

B. Alternate transcript 1

"TESTIS EXON 1"

```
  1  CTGCGGATGCCACGGAACATCGAGCCAAATCCCAGGAACACGCTCTGAACCCCAGGAGCT   60
                              | "TESTIS EXON 1A"
 61  GCACACCACTCTATTAGGCCCAGGACGGAGAAGGAGGCGTCCTGCTCCTGCCAGCCTTAA  120
121  GATGGGAATTTTAGGGTCTGGACATCACTGGTGCTCCAGGTCAGCTTTCCTGGTTGCAGA  180
                                                      | EXON 2
181  TCTCTCCTGGTCAAGGCTCCCAGCTCGCCTGGATCCCACAACTGCACAGTGTCCCGCCCA  240
            *
241  GGAGTGAAGGATG .....  253
```

C. Alternate transcript 2

"TESTIS ALTERNATE EXON 1"

```
  1  CTGCGGATGCCACGGAACATCGAGCCAAATCCCAGGAACACGCTCTGAACCCCAGGAGCT   60
 61  GCACACCACTCTATTAGGTAGTTTATTGGCGCATCAAATCTGGAGTCTACCTCCCTCGGT  120
121  TCACAAATCAGTTCAGAGAGGATCAAACTTGCCCAAGATTAAAGAGTAATGGTGTCAC    180
181  CTGCTCCTCTTCCCTGAATGGCATGATGCCAGGGATGTGACTGGTGACCTGAAAGGGAGG  240
241  GAAATCAAGGCAGGAACGGCTGGGTGTGATGGAGACCTCAAGGCTGTTGTGAGCCCCCCA  300
301  AGAACAGACTCTCTGGAGGCAGGCTTTATCGAGCAGGTCGTTCAACTGGGGAGCACAAAG  360
361  GCTACTTAAATTTTTGGGGAGTGAGTAGGGGCACTCAGGGCAAACGGATGTCATTGTCCA  420
421  AGACCAAGGTGTAGGGAATGCTTTACTGCATGAAAAGGAATTTGAGGTGCTTGCTGTCTG  480
481  GACGTGACTTTGTCCAGAGAGGAAATTTAACCTATAACCTGGCCACCGGTTATGACTACC  540
541  TCAAGGATTGCAGAGGTGGGGCCAAAAGGCTATGTACGTGCTCTGGAACATGCAGGCCCA  600
601  GGACGGAGAAGGAGGCGTCCTGCTCCTGCCAGCCTTAAGATGGGAATTTTAGGGTCTGGA  660
661  CATCACTGGTGCTCCAGGTCAGCTTTCCTGGTTGCAGATCTCTCCTGGTCAAGGCTCCCA  720
                                 | EXON 2          *
721  GCTCGCCTGGATCCCACAACTGCACAGTGTCCCGCCCAGGAGTGAAGGATG .....  771
```

Fig. 7

```
-660  GAACTGCCTTCCTGGATGAGGACTGCATGAGCAGAGACCTGGTGATGGGAGCCCACTAAG  -601
-600  GCCTGCCGGAGGAGCTAGAAGTAGAAGCAGGAACCACTGGAGCTGAGTCTCCTCTCTCCA  -541
-540  GATGCCACAGCCTGTCAGAAGCGGGACTCGGGAAAAGGGCTTCTCTTCCGCCCCAGGACA  -481
-480  GAGTCTGTTTTGTTTCTCGCCTACTCTGTCTGGCTCCTCTCCAACACCAGTTCTTAAGGC  -421
-420  TCTGGACATACACAATTCCACAGGCCCCTCTCCCAGGATCCAGAAACAGGACAGTCACAT  -361
-360  CCGGCATCCTCTGCCAACCCCGGCTCCTCCAGCTTCATCGCAGTCCTCAGTCCCTGGCAA  -301
-300  CCACCCACCGAATCCCCTTCCCTGCCACCGTGTGTGGAAGCGGGATACTGGACAGTCATT  -241
-240  TTAGCTGATTTGTTCAATTTGTTTCCTGAGCTTTGGGCAACCCACTCCATCTGTAGATGG  -181
-180  CTGTAAGCAACTTCCAAGCAGCATGCCTTCCTAGCCACCTCCCAGGAGCTCCCCAAGGGC  -121
-120  TGCCTTTCATTCTCCTTCCAGGGGTCTGTAGAATACAGCCCTGGATGTTTCCAAGGCACG  -61
             *
 -60  GACTGGCATAATAAGCGCAGGCGTCTCCATGACACCGTTCATTGAGCTTATTGGAGCGTT  -1
           *      *
   0  CTGCGGATGCCACGGAACATCGAGCCAAATCCCAGGAACACGCTCTGAACCCCAGGAGCT  59
  60  GCACACCACTCTATTAG  76
```

Fig. 9

A
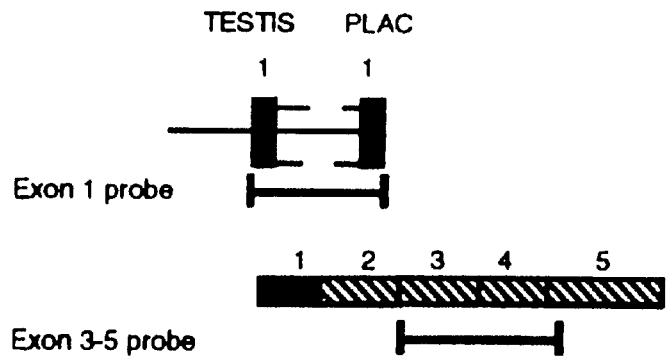
B
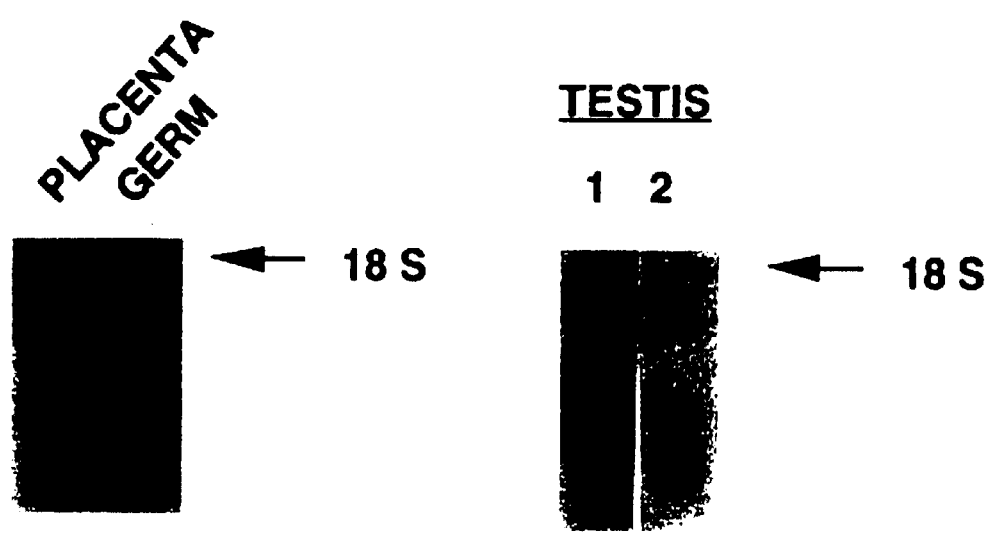
Fig. 10

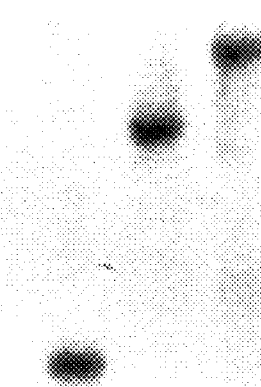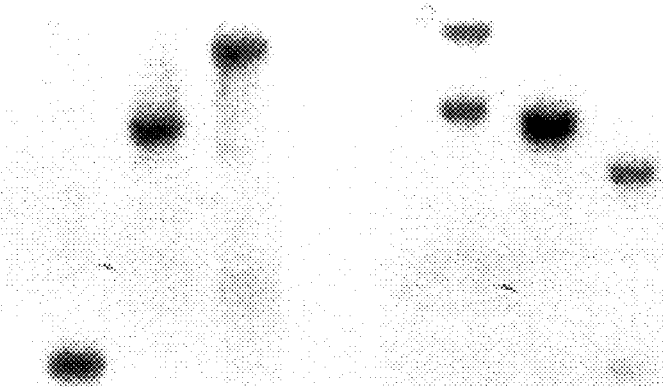
Fig. 11

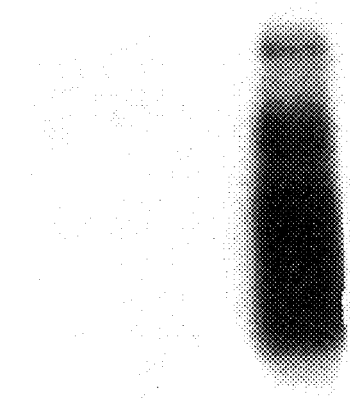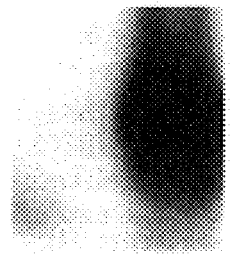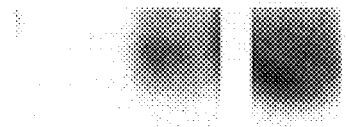
Fig. 12

5'→AGCCTCGAGAATTCATGCTGCTCTGGGTGCTCTTTGTGATCCTCATCCTCACCAGTGGCTC
CCACTGCTCATCACTGCCCCCCTCACCTGCCCCTTCAGGATGCAGCGACAGGAAGACAGCATGTG
GACAGAGGACAAGCAGATGACCCTGGAGAGCATCTTGCAGGGATTCCCAAGGATGAAGCCTT
CAGCGGGACGCTTGAGTCGACCCGG→3'

*Fig. 17*

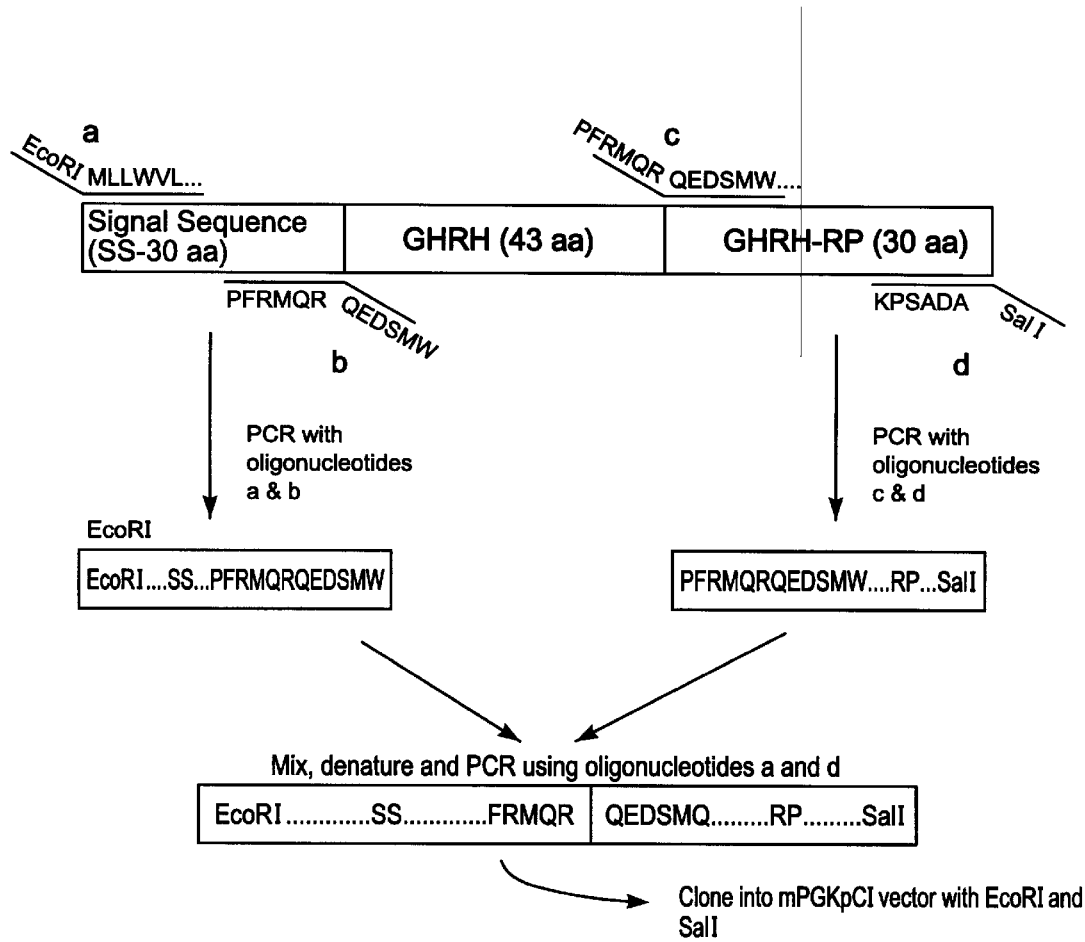
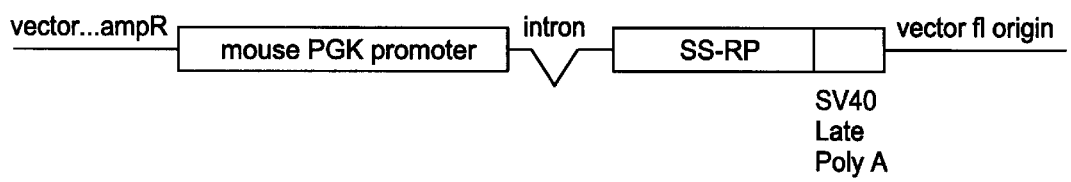
Fig. 18

USE OF GHRH-RP TO STIMULATE STEM CELL FACTOR PRODUCTION

REFERENCE TO RELATED APPLICATION

This application claims priority upon U.S. patent application Ser. No. 60/008,933 filed Dec. 20, 1995, which is hereby incorporated by reference in its entirety.

This invention was made with support from NIH Grant Nos. RO1 DK41899, and KO4 DK02042. The government has certain rights in the invention.

BACKGROUND

The present invention relates generally to biotechnology, and in particular to novel uses and production of Growth Hormone Releasing Hormone Related Peptide (GHRH-RP).

As further background, Growth Hormone Releasing Hormone (GHRH) is known to be the hypothalamic factor that stimulates the release of pituitary growth hormone. Rat GHRH mRNA and peptide have been identified in multiple tissues outside of the hypothalamus including gut, placenta and gonads. M. O. Thorner et al., *Acta Endocrinol* [Suppl] (Copenh) 276, 34 (1986); T. O. Bruhn, R. T. Mason, W. Vale, *Endocrinology* 117, 1710 (1985); O. H. Pescovitz, N. Johnson, S. A. Berry, Pediatr. Res. 29, 510 (1990); G. Meigan, A. Sasaki, K. Yoshinaga, *Endocrinology* 123, 1098 (1988); A. Bagnato, C. Moretti, J. Ohnishi, G. Frajese, K. J. Catt, *Endocrinology* 130, 1097 (1992); S. A. Berry and O. H. Pescovitz, *Endocrinology* 123, 661 (1988). Southern blot analysis of rat genomic DNA indicates that there is a single GHRH gene. Alternate first exons are used to regulate differential GHRH mRNA transcription in various tissues. K. E. Mayo, G. M. Cerelli, M. G. Rosenfeld, R. M. Evans, *Nature* 314, 464 (1985); Gonzalez-Crespo and A. Boronat, *Proc. Natl. Acad. Sci. USA* 88, 8749 (1991); C. H. Srivastava, B. S. Monts, J. K. Rothrock, M. J. Peredo, O. H. Pescovitz, *Endocrinology* 136, 1502 (1995). Exons 2 through 5 are common to all tissues and encode for a 104 amino acid GHRH precursor peptide. This peptide is cleaved into a 29 amino acid N-terminal signal peptide, the mature 43 amino acid GHRH peptide, and a putative 30 amino acid C-terminal peptide, referred to as GHRH-Related Peptide (GHRH-RP).

GHRH is postulated to have arisen from a single ancestral gene approximately 1250 million years ago. R. M. Campbell and C. G. Scanes, *Growth Regulation* 2, 175 (1992). This gene is believed to give rise to the various GHRH family members including glucagon, secretin, pituitary adenylate cyclase activating peptide (PACAP), and vasoactive intestinal peptide (VIP). While the other members of this family are known to produce more than one functional peptide from their precursor proteins, exon loss was hypothesized to explain the occurrence of a single peptide product for both the GHRH and secretin genes. R. M. Campbell and C. G. Scanes, *Growth Regulation* 2, 175 (1992). Pre-pro-VIP produces both peptide histidine isoleucine and VIP and proteolytic cleavage of the PACAP precursor produces PACAP-related peptide and PACAP.

The GHRH mRNA and peptide and other members of the GHRH family have previously been identified in testicular tissue. S. A. Bery, C. H. Srivastava, L. R. Rubin, W. R. Phipps, O. H. Pescovitz, *J. Clin. Endo. Metab.* 75, 281 (1992); M. Ohta, S. Funakoshi, T. Kawasaki, N. Itoh, *Biochem. Biophys. Res. Comm.* 183, 390 (1992); S. Shioda et al., *Endocrinology* 135, 818 (1994); R. Hakanson, F. Sundler, R. Uddman, in *Vasoactive Intestinal Peptide*, S. Said, Ed. (Raven Press, New York 1982), pp. 121–144. The GHRH transcript is localized to spermatogenic cells, is developmentally regulated and is actively transcribed during the onset of spermatogenesis. C. H. Srivastava et al., *Endocrinology* 133, 83 (1993); S. A. Berry and O. H. Pescovitz, *Endocrinology* 127, 1404 (1990). Northern blot analysis of RNA from separated testicular cells demonstrates the highest amounts of GHRH mRNA in spermatocytes and immature round spermatids. GHRH mRNA is not present in more mature elongating spermatids and epididymal sperm. Using immunohistochemical analysis, the GHRH peptide is localized to both germ cells (O. H. Pescovitz et al., *Endocrinology* 127, 2336 (1990)) and Leydig cells (T. Ciampani, A. Fabbri, A. Isidori, M. L. Dufau, *Endocrinology* 131, 2785 (1992); A. Fabbri, D. R. Ciocca, T. Ciampani, J. Wang, M. L. Dufau, *Endocrinology* 136, 2303 (1995)). A GHRH receptor is transcribed in rat Sertoli cells (C. H. Srivastava et al., *Endocrine Journal*. 2, 607 (1994)) and treatment of cultured Sertoli cells with GHRH activates Sertoli cell c-fos and stem cell factor gene expression (C. H. Srivastava, P. R. Breyer, J. K. Rothrock, M. J. Peredo, O. H. Pescovitz, *Endocrinology* 133, 1478 (1993)). Both of these Sertoli cell products are crucial for the normal progression of spermatogenesis. R. S. Johnson, B. M. Spiegelman, V. Papaioannou, *Cell* 71, 577 (1992); K. M. Zsebo et al., *Cell* 63, 213 (1990); E. Huang et al., Cell 63, 225.

In the area of fertility management, the literature has taught the treatment of human female infertility by administration of gonadotropins such as follicle stimulating hormone (FSH) combined with luteinising hormone (LH), and the the addition of GHRH to this mixture to improve the therapy. Tests have also been derived to predict whether the FSH/LH/GHRH regimen will benefit the patient. See, e.g., U.S. Pat. No. 5,175,111. In this area it is also known that inhibition of FSH, for example with FHS-Inhibiting Protein (FSH-IP), can be used to provide contraception in males and females, since FSH is required for maturation of ovarian follicles and testicular spermatogenesis. In addition, disruption of FSH-IP activity, e.g. by administration of antibodies to FSH-IP, has been taught as a means for promoting fertility. See, e.g., U.S. Pat. No. 5,037,805.

SUMMARY OF THE INVENTION

In one feature of the invention, it has been discovered that GHRH-RP specifically activates stem cell factor (SCF), a factor crucial for normal spermatogenesis, in Sertoli cells. Accordingly, methods of the invention involve the use of GHRH-RP in the management or control of fertility in patients, including to stimulate the production of stem cell factor, and spermatogenesis, and the reduction of GHRH-RP activity in Sertoli cells to inhibit production of SCF and spermatogenesis in mammals.

Another embodiment of the invention concerns a pharmaceutical composition for stimulating the production of SCF or promoting spermatogenesis in mammals, including GHRH-RP and a pharmaceutically-acceptable carrier.

The present invention also provides an isolated nucleotide encoding GHRH-RP which is free from the GHRH coding sequence, vectors incorporating such nucleotides, host cells transformed by such vectors, and methods involving culturing the host cells under conditions effective to produce GHRH-RP. Preferably, the nucleotide is a cDNA encoding GHRH-RP and also containing a sequence coding for a leader which facilitates secretion of the encoded polypeptide from the host cell, and a sequence encoding a proteolytic site for cleavage of the polypeptide to remove the leader. The present invention also provides transgenic mammals which overexpress GHRH-RP in all or selected tissues, and which lack expression of GHRH-RP in all or selected tissues.

Still another feature of the present invention concerns the discovery that the GHRH gene, as transcribed in testis, includes not only the five previously-known exons in the gene, but also a sixth exon as a result of alternative splicing. This further exon, which is exon 1 in testis, is located about 700 bp upstream in the genome from that of placental exon 1. The invention thus also provides an isolated polynucleotide including testis exon 1, preferably in addition to the other five known exons in the GHRH gene.

The present invention provides novel methods employing or inhibiting GHRH-RP to manage fertility in mammals, including humans. The methods of the invention are expected to provide new fertility-promoting and contraceptive treatments in humans and other animals. The present invention also provides nucleotides, vectors and host cells for the convenient production of GHRH-RP, and transgenic mammals useful in screening and study of GHRH-RP and related factors. Additional objects, features and advantages of the present invention will be apparent from the following description.

BRIEF DESCRIPTION OF THE FIGURES

The file of this patent contains at least one drawing executed in color. Copies of this patent with color drawings will be provided by the Patent and Trademark Office upon request and payment of the necessary fee.

FIGS. 7 A–C shows the sequences of three alternative GHRH transcripts found in germ cells, as described in Example 5 below. 7A (SEQ ID NO:4), complete sequence of one transcript, with the putative peptide sequence shown (SEQ ID NO:5). The consensus poly(A) addition signal is overlined. The region of sequence heterogeneity adjacent to the poly(A) signal is underlined. 7B (SEQ ID NO:6), alternative transcript containing testis exon 1 spliced to the 3'-portion of placental exon 1 (testis exon 1A). 7C (SEQ ID NO:7), alternative transcript containing the entire sequence of testis exon 1 (boldface type), placental exon 1 (underlined), and the intervening genomic sequence as one contiguous exon 1 sequence. In all three transcripts, the exon boundries are indicated by verticle lines above the letters, and the ATG translation start site is indicated by an asterisk.

FIG. 8A, genomic clones (clones 1 and 23, Example 5) isolated from a λ library. A restriction map of the XhoI fragment containnig the placental and testicular first exons is shown: B, BamHI; E, EcoRI; H, HindIII; X, XhoI. FIG. 8B, proposed structure of the GHRH gene. The exons are numbered. Testis 1A contains most of the sequence of placenta exon 1. Testis alt ex 1 contains the testicular and placenal first exons as well as the entire genomic sequence between them. FIG. 8C, GHRH transcripts in three different tissues:  (light shading)=hypothalamic GHRH exon 1;  (dark shading)=on possible placental GHRH exon 1; ■ (filled)=testicular GHRH exon 1;  (cross-hatch)=GHRH exons 2–5. The dashed lines connect testicular exon 1 and placental exon 1, forming a contiguous exon.

FIG. 9 shows the sequence of the 5' flanking region of testicular GHRH (SEQ ID NO:8), as described in Example 5 below. The 5' transcription initiation site defined by RACE analysis has been designated nucleotide 1. The underlined sequences represent consensus sequences for transcription factor binding; a site 80% homologous to a spermatogenic-specific binding site in the c-mosD gene is located at −517, an SP1 site is located at −493, and sites homologous to those found in the spermatogenesis-specific proenkephalin promoter are found at −210 and −130. A TATA-like sequence is shown in boldface type. Potential transcription initiation sites are indicated by asterisks.

FIGS. 10A and B shows the results of Northern blot analysis of GHRH mRNA in testis and placenta. FIG. 10A, diagram of the exon 1 and exon 3–5 probes used (Example 5, below). FIG. 10B, autoradiograms of blots. Left panel, twenty micrograms of total placenta or germ cell poly(A)+ RNA were hybridized to the 733-bp exon 1 probe described in Example 5. Right Panel, ten micrograms of testicular poly(A)+ RNA wre hybridized to either the testicular exon 1 probe (lane 1) or a GHRH exon 3–5 probe (lane 2).

FIG. 11 shows the results of Southern blot analysis of the rat GHRH gene as described in Example 5. Rat liver DNA was digested with BamHI (B), EcoRI (E), or HindIII (H); subjected to electrophoresis on a 1% agarose gel; transferred to a nylon membrane; and hybridized to either a probe extending from −200 to the 3'end of testicular exon 1 or to a GHRH exon 3–5 probe.

FIG. 12 shows an analysis of GHRH exon 1 in hypothalamus and testis as described in Example 5. RT-PCR was performed on RNA from testicular germ cells (G), hypothalamus (H) or liver (L) using the primers indicated at the left. The PCR products were subjected to electrophoresis on a 1.8% agarose gel, transferred to a nylon membrane, and hybridized to the GHRH exon 3–5 probe.

FIG. 17 shows the sequence of the PCI vector with the SS-RP insert (SEQ ID NO:9), as described in Example 6 below. EcoRI and SalI were used for cloning. The sequence is precisely as predicted. SS-RP sequencing is underlined.

FIG. 18 is a schematic diagram illustrating the production of transgenic mammals in accordance with the invention, as described in Example 7 below.

DESCRIPTION OF THE PREFERRED EMBODIMENTS

For the purposes of promoting an understanding of the principles of the invention, reference will now be made to preferred embodiments thereof and specific language will be used to describe the same. It will nevertheless be understood that no limitation of the scope of the invention is thereby intended, such alterations and further modifications in the invention, and such further applications of the principles of the invention as described therein being contemplated as would normally occur to one skilled in the art to which the invention relates.

As discussed above, one aspect of the present invention concerns regulating intratesticular stem cell factor (SCF) levels and/or spermatogenesis in a mammal by regulating the level of GHRH-RP. As discussed in more detail below, it has been discovered that GHRH-RP stimulates the production of SCF in Sertoli cells, a factor which is required for spermatogenesis. Accordingly, it is expected that spermatogenesis can be promoted by increasing the intratesticular level of GHRH-RP, e.g. by the administration of GHRH-RP peptide preparations or the overexpression of a nucleotide encoding GHRH-RP. It is also expected that spermatogenesis can be inhibited or eliminated by decreasing the intratesticular level of active GHRH-RP, e.g. by the administration of antibodies to GHRH-RP, the knock-out or down-regulation of a mammal's expression of its GHRH-RP DNA, by anti-sense RNA to the GHRH-RP mRNA, by competitive antagonists or agonists to GHRH-RP binding, or by otherwise interfering with the processing of the GHRH pre-protein to biologically active GHRH-RP.

Figure 1:
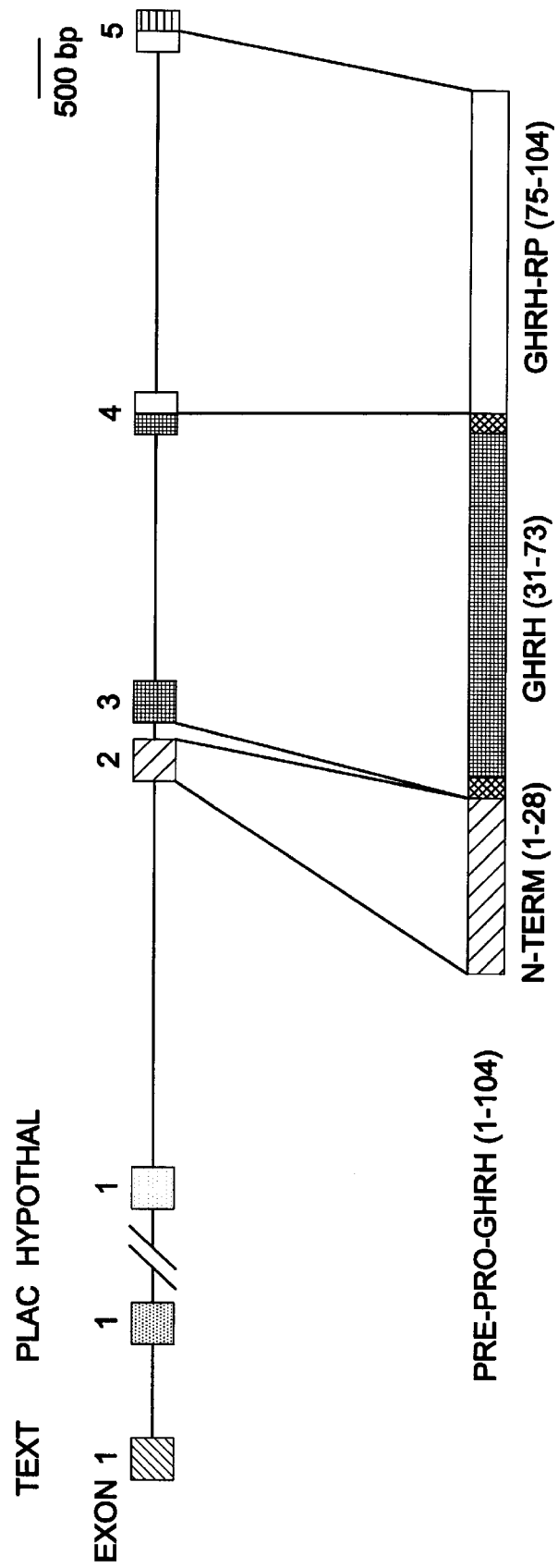
FIG. 1 is a schematic diagram which illustrates the structure of the rat GHRH gene and the GHRH precursor peptide.

As further background information concerning GHRH-RP, Southern blot analysis of genomic DNA indicates that there is a single GHRH gene. In particular, FIG. 1 shows the structure of the rat GHRH gene and the GHRH precursor peptide. The rat GHRH gene consists of 5 exons with alternate first exons for testis (TEST), placenta (PLAC) and hypothalamus (HYPOTHAL). Exons 2 through 5 encode the GHRH precursor peptide in all tissues studied to date. Subsequent processing of the precursor peptide yields a 29 amino acid N-terminal signal peptide, the mature 43 amino acid GHRH and a 30 amino acid C-terminal peptide, GHRH-RP. Alternate first exons are used to regulate differential GHRH mRNA transcription in various tissues. K. E. Mayo, G. M. Cerelli, M. G. Rosenfeld, R. M. Evans, *Nature* 314, 464 (1985). Gonzalez-Crespo and A. Boronat, *Proc. Natl. Acad. Sci. USA* 88, 8749 (1991); C. H. Srivastava, B. S. Monts, J. K. Rothrock, M. J. Peredo, O. H. Pescovitz, *Endocrinology* 136, 1502 (1995).

Specifically, the amino acid sequences of specific GHRH-RP peptides useful in the present invention are given below:

```
SEQ ID NO:1 Human
Gln Val Asp Ser Met Trp Ala Glu Gln Lys Gln Met Glu 13
 1               5                  10

Leu Glu Ser Ile Leu Val Ala Leu Leu Gln Lys His Ser 26
        15              20                  25

Arg Asn Ser Gln Gly                                  31
                30

SEQ ID NO:2 Mouse
Gln Glu Asp Ser Met Trp Thr Glu Asp Lys Gln Met Thr 13
 1               5                  10

Leu Glu Ser Ile Leu Gln Gly Phe Pro Arg Met Lys Pro 26
        15              20                  25

Ser Ala Asp Ala                                      30
                30

SEQ ID NO:3 Rat
His Leu Asp Arg Val Trp Ala Glu Asp Lys Gln Met Ala 13
 1               5                  10

Leu Glu Ser Ile Leu Gln Gly Phe Pro Arg Met Lys Leu 26
        15              20                  25

Ser Ala Glu Ala                                      30
                30
```

In addition to native forms of the GHRH-RP polypeptides, the present invention also concerns the use of polypeptides having amino acid sequences similar to those of the native polypeptides, but into which modifications are naturally provided (e.g. allelic variations in the nucleotide sequence which may result in amino acid changes in the polypeptides) or deliberately engineered. Modifications of interest in the sequences may include the replacement, insertion or deletion of one or more amino acid residues in the coding sequence. For example, the modified polypeptide may contain one or more additional amino acids, at one or both ends of the polypeptide chain; may have an amino acid sequence which differs from that of the naturally-occurring polypeptide; or may be an active fragment of the naturally-occurring polypeptide.

Illustrative modifications which may be undertaken include, for example, substituting one polar amino acid, such as glycine for another polar amino acid; or one acidic amino acid, such as aspartic acid, may be substituted for another acidic amino acid such as glutamic acid; or a basic amino acid, such as lysine, arginine or histidine may be substituted for another basic amino acid; or a non-polar amino acid, such as alanine, leucine or isoleucine may be substituted for another non-polar amino acid.

The term "substantially identical" is used herein to encompass such potential modifications, and specifically herein means that a particular subject sequence, for example, a mutant sequence, varies from the native sequence by one or more substitutions, deletions, or additions, the net effect of which is to retain biological activity of the native peptide. Alternatively, DNA analog sequences are substantially identical to the specific DNA sequences disclosed herein if: (a) the DNA analog sequence is derived from substantially the entire coding regions of the native mammalian GHRH-RP genes; or (b) the DNA analog sequence is comparable in length with and capable of hybridization to DNA sequences of (a) under moderately stringent conditions (defined in Sambrook et al., *Molecular Cloning: A Laboratory Manual*, 2Ed. Vol. 1, pp. 101–104, Cold Spring Harbor Laboratory Press (1989) as including the use of a prewashing solution of 5×SSC, 0.5% SDS, 1.0 mM EDTA (pH 8.0) and hybridization conditions of about 55° C., 5×SSC, overnight) and which encode biologically active GHRH-RP molecules; or (c) DNA sequences which are degenerate as a result of the genetic code to the DNA analog sequences defined in (a) or (b) and which encode biologically active GHRH-RP molecules. Preferred substantially identical analog polypeptides will be greater than about 80 percent similar to the corresponding sequence of the native protein, and in particular in the case of GHRH-RP to the more highly-conserved sequence including amino acids 1 to 19. Sequences having lesser degrees of similarity but comparable biological activity are considered to be equivalents. In defining nucleic acid sequences, all subject nucleic acid sequences capable of encoding substantially similar amino acid sequences are considered substantially similar to a reference nucleic acid sequence.

Percent similarity may be determined, for example, by comparing sequence information using the GAP computer program, version 6.0, available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math.* 2:482,1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a uniary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps. In the text herein, including the claims, the percent similarly calculated using the GAP program with the above-identified preferred default parameters will be referred to as percent similarity "as determined by the GAP program".

Thus, in a preferred aspect of the invention the GHRH-RP polypeptide used will be encoded by a DNA sequence selected from:

(a) the coding region of a native GHRH-RP gene;

(b) a DNA sequence which hybridizes under moderately stringent conditions to the DNA of (a) and encodes a polypeptide which stimulates the production of SCF in Sertoli cells; and (c) a DNA sequence that encodes a polypeptide having the amino acid sequence of the polypeptides encoded by the DNA sequences of (a) and (b).

Preferred polypeptides for use in the invention are thus provided having an amino acid sequence selected from:

(a) an amino acid sequence of a native GHRH-RP polypeptide; or (b) an amino acid sequence that is substantially identical to (a).

Figure 2:
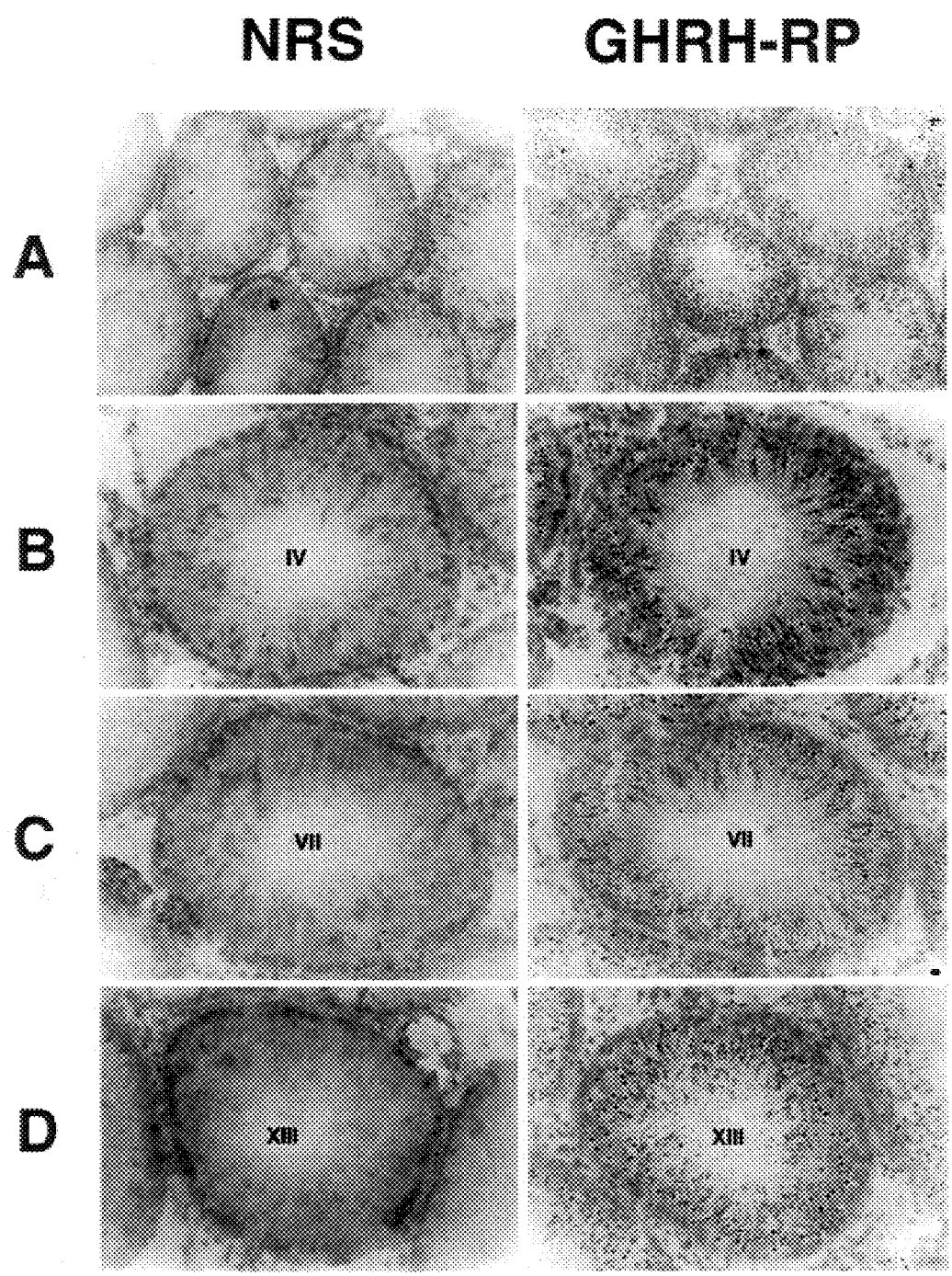
FIGS. 2 A–D are photomicrographs depicting the immunohistochemical localization of GHRH-RP in adult rat testis.

In specific work to date, to test for the presence of a putative GHRH-RP peptide, antisera were generated by BSA-conjugating rat GHRH-RP and immunizing rabbits with 500 mg of GHRH-RP in Complete Freunds Adjuvant. Booster injections of 250 mg GHRH-RP in Incomplete Fruends Adjuvant and GHRH-RP antisera were characterized by ELISA. The antisera, which did not cross-react with GHRH, VIP, PCAP, Secretin, PHI or glucagon ($\leq 1$ mg), were used in immunohistochemistry performed on testes of adult rats as described in Example 1 below. Abundant GHRH-RP immunoactivity was present in the acrosomes at nearly all stages of germ cell development as illustrated in FIGS. 2A–D. To generate the photomicrographs shown, rat seminiferous tubules were incubated with preimmune rabbit sera (NRS) on the left and GHRH-RP specific antisera on the right. (A) 100× magnification of several different stage tubules. 200× magnification of a single seminiferous tubule at (B) Stage IV, (C) Stage VII, and (D) Stage XIII. Intense specific staining predominated in stage IV seminiferous tubules in the pachytene primary spermatocytes, step 4 secondary spermatocytes and step 17 elongating spermatids (FIG. 2B).

Figure 4:
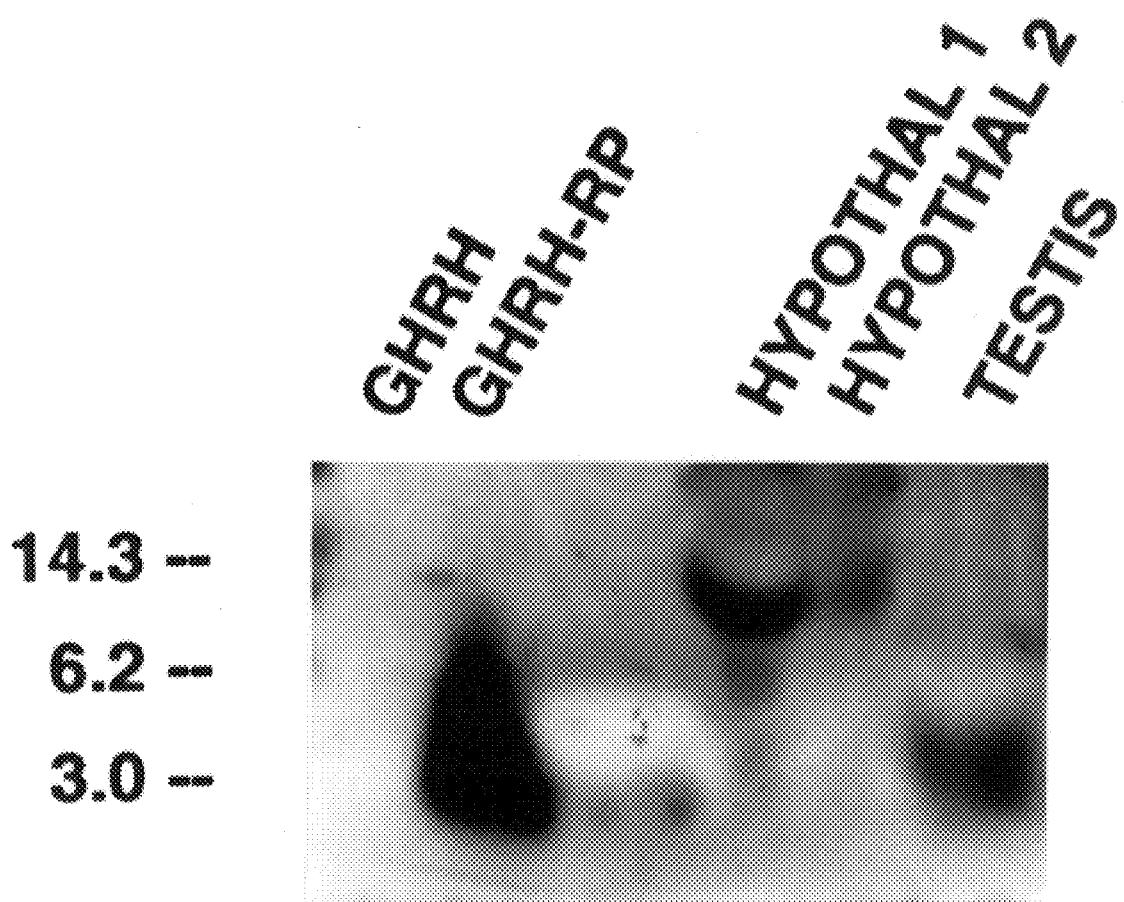
FIG. 4 shows Western gel analysis of rat hypothalamus and testis tissue extracts.

To estimate the size of the peptide identified in testis, Western gel analysis was performed as described in detail in Example 2 below. Briefly, FIG. 4 shows the results of experiments in which SDS-PAGE was performed and GHRH-RP antigen-antibody complex revealed by chemiluminescence. Controls were synthetic GHRH (100 ng) and synthetic GHRH-RP (100 ng). The sample is shown as (TESTIS) (2 mg). Protein molecular mass markers are indicated on the left. Using the GHRH-RP antisera that did not recognize GHRH (FIG. 4), a band of approximately 3.5 kDa was seen in the GHRH-RP control lane as expected. In testis a 3.5 kDa band predominated that was consistent with the size of synthetic GHRH-RP (FIG. 4) suggesting that in testicular germ cells the GHRH precursor peptide is not stored.

Figure 5:
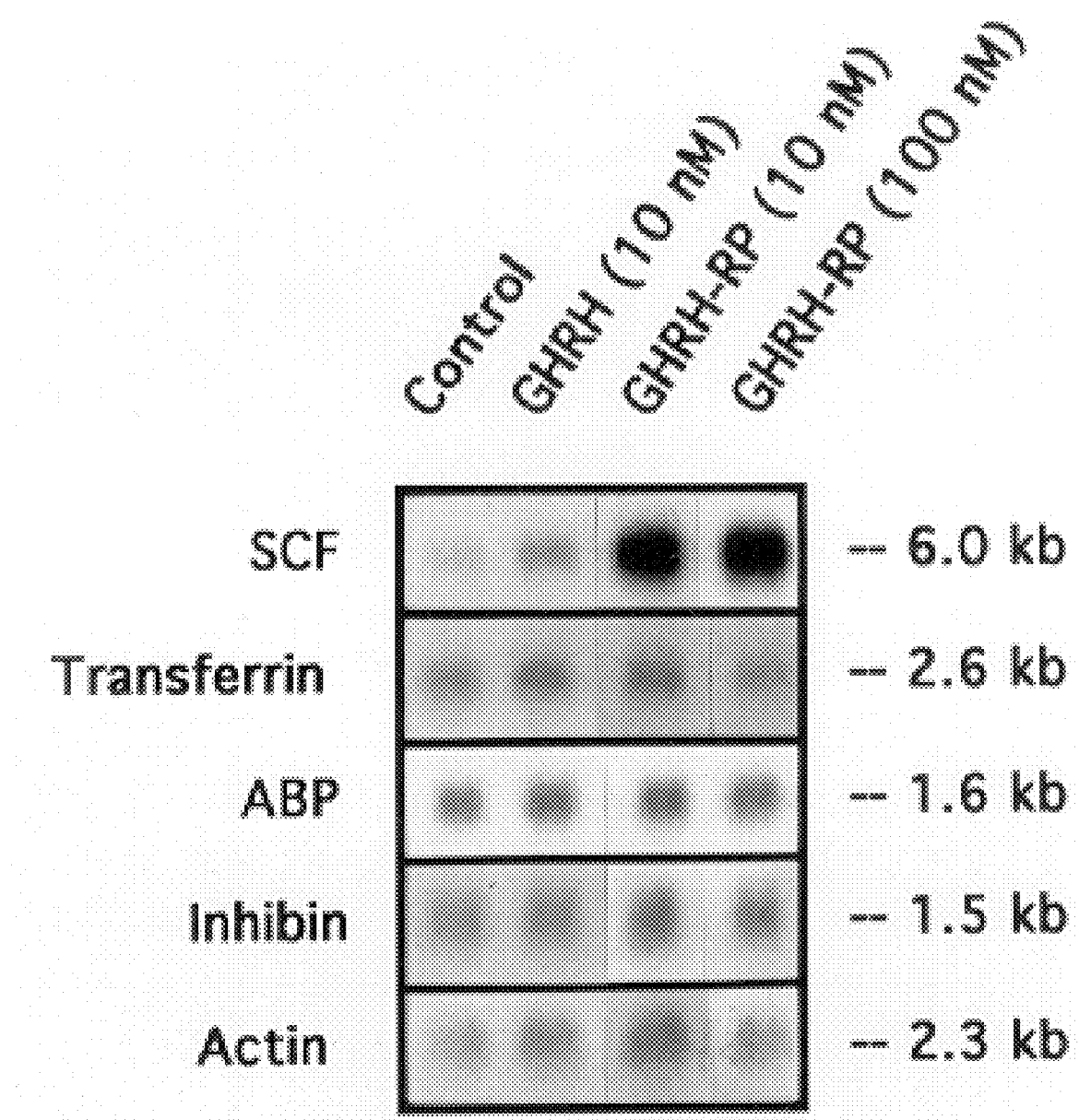
FIG. 5 shows Northern blot analysis of GHRH-RP specific Sertoli cell gene expression.
Figure 6:
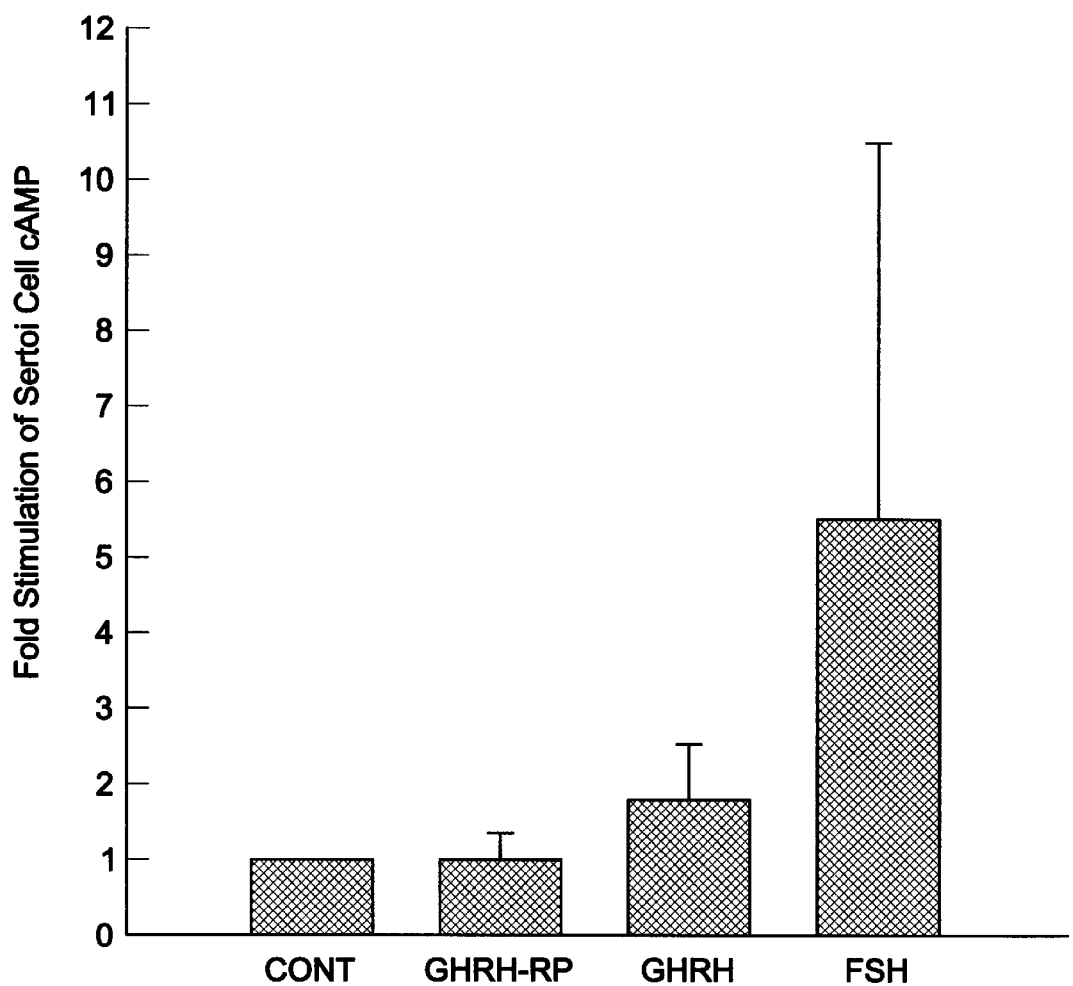
FIG. 6 is a graph illustrating the stimulation of adenylate cyclase in cultured Sertoli cells.

As indicated above, it has been discovered that GHRH-RP has a unique testicular action. GHRH-RP specifically activated SVF in Sertoli cells as described in Example 3 below. Briefly, FIG. 5 shows the results of work in which Rat Sertoli cells, isolated and cultured for 4 days were treated with rat GHRH-RP (10 nM and 100 nM), rat GHRH (10 nM) or control media for 16 hours. Northern gel analysis of 10 $\mu$g of total Sertoli cell RNA was performed and the blot probed for SCF, transferrin, androgen binding protein (ABP), $\alpha$-inhibin and $\gamma$-actin as control. B. Bloch, A. Baird, N. Ling, R. Guillemin, Endocrinology 118, 156 (1986). Stimulation of SCF expression is 12 fold over control at 10 nM and 16 fold at 100 nM concentrations of GHRH-RP. GHRH (10 nM) stimulated stem cell factor gene expression 3 fold over control. There was no stimulation of transferrin, ABP or $\alpha$-inhibin gene expression over control using GHRH-RP or GHRH. Other Sertoli cell specific transcripts including transferrin, ABP and $\alpha$-inhibin were note regulated by GHRH-RP (FIG. 6). Although a functional GHRH receptor has been identified in Sertoli cells (R. S. Johnson, B. M. Spiegelman, V. Papaioannou, Cell 71, 577 (1992); K. M. Zsebo et al., Cell 63, 213 (1990); E. Huang et al., Cell 63, 225), the GHRH-RP stimulation of stem cell factor expression may not be mediated through this receptor. Unlike GHRH, GHRH-RP does not stimulate increases in adenylate cyclase in cultured Sertoli cells, as demonstrated in Example 4 below. Briefly, shown in FIG. 6 are the results of experiments in which rat Sertoli cells, isolated and cultured for 4 days were incubated with GHRH-RP (100 nM), GHRH (100 nM), FSH (0.0275 U/ml) or control media for 30 minutes at 37° C. The cells were then assayed for cAMP production by 125 I cAMP Radioimmunoassay. C. H. Srivastava, J. D. Fleck, A. M. Meyers, S. A. Berry, O. H. Pescovitz, "Distribution of Growth Hormone Releasing Hormone-Like (HRH-LI) mRNA and Immunoreactivity in Rat Tissues" (Abstract), The *Endocrine Society,* 73rd Annual Endocrine Society, Washington, D.C. (1991). Adenylate cyclase stimulation is measured as fold stimulation of control. Each bar is representative of five separate experiments.

As to the production of GHRH-RP polypeptides for use in the invention, nucleic acid sequences encoding the polypeptides may be constructed using standard recombinant DNA technology, for example, by cutting or splicing nucleic acid sequences using restriction enzymes and DNA ligase. Alternatively, nucleic acid sequences may be constructed using chemical synthesis, such as solid-phase phosphoramidate technology. Polymerase chain reaction (PCR) may also be used to accomplish splicing of nucleic acid sequences by overlap extension as known in the art.

The segment of the polynucleotide chain which encodes GHRH-RP is, of course, designed according to the genetic code; however, because of the degeneracy of the genetic code, a wide variety of codon combinations can be selected to form the polynucleotide chain which encodes the product polypeptide. It is known that certain specific codons are more efficient for expression in certain types of organisms, and the selection of codons can be made according to those codons which are most efficient for expression in the type of organism to serve as focus for the recombinant vector. Nonetheless, any correct set of codons will encode the desired product. Codon selection may also be dependent upon considerations of vector construction, e.g. it may be necessary to avoid inserting a restriction site in the polynucleotide chain if the vector is to be later manipulated with a corresponding restriction enzyme, or if the ultimate host organism produces the corresponding restriction enzyme.

As is conventional, the polynucleotide chain containing the GHRH-RP sequence can also contain linkers at its ends to facilitate insertion and to restriction sites in a cloning vector. The polynucleonic tide chain may also encode a fusion polypeptide and when so constructed will usually contain terminal sequences encoding amino acid sequences serving as proteolytic processing sites, whereby the GHRH-RP polypeptide may be proteolitically cleaved from the remainder of the fusion peptide. Other conventional sequences may also be included, e.g. appropriate start and stop signals.

DNA encoding GHRH-RP polypeptides for use in the invention can be conventionally incorporated into viral, plasmid or other vectors and used to transform host cells to achieve expression of the polypeptide in the cells. The hybrid DNA molecules are expressed by operatively linking them to an expression control sequence in an appropriate expression vector, which in turn is used to transform an appropriate unicellular host. The operative linking of a hybrid DNA sequence of this invention to an expression control sequence includes the provision of a translation start signal in the correct reading frame upstream of the DNA sequence. Therefore, a coding sequence is "operatively linked to" another coding sequence when RNA polymerase will transcribe the coding sequence into mRNA which is then translated into a polypeptide.

In selecting an expression control sequence, a variety of factors should also be considered. These include, for example, the relative strength of the system, its controllability, and its compatibility with the particular DNA sequence, of this invention, particularly as regards potential secondary structures. Unicellular hosts should be selected by consideration of their compatibility with the chosen vector, the toxicity of the product coded on expression by the DNA sequences of this invention to them, their secretion characteristics, their ability to fold proteins correctly, their stability and culturing requirements, and the ease of purification of the products coded on expression by the DNA sequences of this invention.

Illustrative suitable host cells for GHRH-RP polypeptide expression include, for example, prokaryotic and eukaryotic cells. Appropriate cloning and expression vectors for use with bacterial, fungal, yeast, and mammalian cellular hosts are described, for example, in Pouwels et al. *Cloning Vectors:A Laboratory Manual,* Elsevier, New York, (1985).

Prokaryotes include gram negative or gram positive organisms, for example, *E. coli* or Bacilli. Suitable prokaryotic host cells for transformation include, for example, *E. coli, Bacillus subtilis, Salmonella typhimurium,* and various other species within the genera Pseudomonas, Streptomyces, and Staphylococcus.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct en expression vector using pBR322, an appropriate promoter and a flt3-L DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning:A Laboratory Manual,* Cold Spring Harbor Laboratory, p. 412, 1982).

Flt3-L polypeptides alternatively may be expressed in yeast host cells, preferably from the Saccharomyces genus (e.g., *S. cerevisiae*). Other genera of yeast, such as Pichia, *K. lactis* or Kluyveromyces, may also be employed. Yeast vectors will often contain an origin of replication sequence from a 2 m yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene*, 107:285–195 (1991); and van den Berg et. al., *Bio/Technology*, 8:135–139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Ampr gene and origin of replication) into the above-described yeast vectors.

The yeast α-factor leader sequence may be employed to direct secretion of the flt3-L polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Illustrative eukaryotic host cells which may be used for polypeptide expression include, for example, yeast cells, CHO, R1.1, B-W and L-M cells, African green monkey cells (including COS1, COS7, BSC1, BSC40, and BMT110 cells), and human cells (including erythroblasts, monocytes, myeloids, T-lymphocytes, B-lymphoblastoid cells, smooth muscle cells, endothelial cells, Sertoli cells, fibroblasts, etc.), and cell lines developed from the foregoing. These cells can be cultured in accordance with conventional procedures known to the art and literature, and the polypeptides produced can likewise be recovered and purified conventionally.

The present invention is not intended to be limited by the choice of vector or host cell. It should of course be understood that not all vectors and expression control sequences will function equally well to express the DNA sequences of this invention. Neither will all hosts function equally well with the same expression system. However, one of skill in the art may make a selection among these vectors, expression control sequences, and hosts without undue experimentation and without departing from the scope of this invention.

The present invention also provides pharmaceutical compositions for stimulating Sertoli cell SCF production and spermatogenesis which include GHRH-RP polypeptides as discussed above. Compositions of this invention, for promoting spermatogenesis, will generally include a therapeutically effective amount of a GHRH-RP polypeptide in a pharmaceutically acceptable carrier. The term "therapeutically effective amount" refers to an amount of protein which will stimulate spermatogenesis. The precise dosage necessary will vary with the age, size and condition of the patient, the nature and severity of the disorder to be treated, and the like. Thus, a precise effective amount cannot be specified in advance and will be determined by the care giver. Appropriate amounts may be estimated by routine experimentation with animal models.

Any pharmaceutically-acceptable carrier which is compatible with the active ingredients is contemplated. Pharmaceutically-acceptable carriers include for instance insert solid diluents or fillers, sterile aqueous solution and various organic solvents. The use of such carriers is well known in the art. In this regard, the phrase "pharmaceutically acceptable" refers to molecular entities and compositions that are physiologically tolerable and do not typically produce an allergic or similar untoward reaction, such as gastric upset, dizziness and the like, when administered to a human. Pharmaceutical compositions, formed by combining a GHRH-RP polypeptide and pharmaceutically-acceptable carriers, are then easily administered in a variety of dosage forms such as injectable solutions.

Particularly for parental administration, solutions of the protein in oils such as sesame or peanut oil, aqueous propylene glycol, or in sterile aqueous solution (desirably isotonic) may be employed. These aqueous solutions are especially suitable for intravenous, intramuscular, subcutaneous and intraperitoneal administration. In this connection, sterile aqueous media which can be employed will be known to those of skill in the art in light of the present disclosure.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about sterile preparation and by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions can be prepared by incorporating the GHRH-RP polypeptide in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the GHRH-RP polypeptide plus any additional desired ingredient from a previously sterile filtered solution thereof.

Pharmaceutical compositions of the invention may be administered in any suitable manner, including for instance potentially parenteral, sublingual, intratesticular, and intrapulmonary. Parenteral administration includes, for instance, intramuscular, subcutaneous, intravenous, intraarterial and intraperitoneal administration. In one preferred mode the GHRH-RP composition will be administered via the testis.

In addition, in accordance with the invention, GHRH-RP may be co-administered with other therapies for increasing fertility, including for instance the administration of gonadotropins or gonadotropin releasing factors, e.g. human chorionic gonadotropin, human menopausal gonadotropin, FSH, or gonadotropin releasing hormone, or of a synthetic androgen, activin (see e.g. U.S. Pat. No. 5,166,190), or the like. In this regard, GHRH-RP may be administered along with or separately from these other therapeutics, and before, simultaneously or after the administration of the other fertility therapies.

The present invention also provides monoclonal or polyclonal antibodies to GHRH-RP, which are useful in immunohistochemical studies and in inhibiting GHRH-RP in vivo to reduce a mammal's production of stem cell factor in Sertoli cells and inhibit spermatogenesis. Such antibodies can be conventionally raised in appropriate mammals such as rabbits. In addition, standard hybridoma technology can be employed to produce monoclonal antibodies to GHRH-RP, if desired. Antibodies to GHRH-RP can also be conjugated to suitable imaging agents such as x-ray, MRI, or PET imaging agents, and administered to mammals, e.g. intratesticularly, to enable externally-generated imaging of GHRH-RP localization and relative levels in the testis, particularly germ cells. Such protocols may be used to provide useful research and screening for any GHRH-RP abnormalities.

The present invention also provides a transgenic mammal all or some cells of which express (preferably over-express) introduced DNA encoding the GHRH-RP peptide, and transgenic mammals all or some cells of which lack expression of the GHRH-RP peptide. Such transgenic mammals can be constructed using standard pronuclear injection technique, as specifically described in the Example 6 below. Such mammals may be used, for example, in the study of GHRH-RP function spermatogenesis and other biological functions, e.g. those related to appetite or other functions whose regulation involve the hypothalamus, and in the screening of agents for inhibiting or promoting spermatogenesis and controlling fertility, or for regulating appetite.

In order to promote a further understanding and appreciation of the present invention and its features and advantages, the following specific Examples are provided. It will be understood that these Examples are illustrative, and not limiting, of the invention.

EXAMPLE 1

Preparation of GHRH-RP Peptide

Rat GHRH-related peptide was synthesized from the deduced amino acid sequence (amino acids 74–104) (K. I. Mayo, G. M. Cerelli, M. G. Rosenfeld, R. M. Evans, Nature 314, 464 (1985). Gonzalez-Crespo and A. Boronat, Proc. Natl. Acad. Sci. USA 88, 8749 (1991); C. H. Srivastava, B. S. Monts, J. K. Rothrock, M. J. Peredo, O. H. Pescovitz, Endocrinology 136, 1502 (1995)) in the Biochemistry Biotechnology Facility at Indiana University. The peptide was conjugated to BSA and antisera were produced by N. Beaudry in four rabbits (Hazelton Labs, Vienna, VA). The rabbits were pretreated with pertussis vaccine, followed by 500 $\mu$g GHRH-RP in Complete Freund's Adjuvant, fortified with killed M. Tuberculosis. Multiple intradermal injections were given at dorsal sites. Booster injections of 250 $\mu$g GHRH-RP in Incomplete Freund's Adjuvant were given at three week intervals and the immunized rabbits were bled 10–14 days after each booster. The GHRH-RP antisera were assayed and characterized by ELISA. The antisera were specific for GHRH-RP and did not cross react with rat GHRH, VIP, PACAP, secretin, PHI and glucagon at concentrations up to 1 $\mu$g.

Adult rat testes were frozen in dry ice cold isopenthane and then embedded in Tissue-Tek (Miles Inc., Elkhart, IN). Twelve $\mu$m sections were cut at −20° C. in a Reichert-Jung cryostat and mounted on poly-L-lysine coated slides. The sections were soaked in 4% paraformaldehyde/0.1 M PBS fixative at room temperature for 60 minutes. The brains from adult rats, perfused at sacrifice with 4% paraformaldehyde/ 0.1 M PBS, were sectioned (35 $\mu$m) and the sections floated in 0.1 M PBS containing 0.5* Triton-X. Each tissue was then rinsed with 0.1 M PBS containing 0.5% Triton-X and blocked in the same buffer containing 10% normal goat serum. They were incubated overnight at 4° C. with rabbit anti-GHRH-RP sera at a dilution of 1:2000, followed by sequential 60 minute incubations at room temperature with the second antibody, biotinylated goat anti-rabbit IgG (1:200), and substrate, avidin DH-biotin-peroxidase complex (Vector Laboratories, Burlingame, Calif.). Each step was followed by three 10 minute washes with 0.1 M PBS containing 0.5% Triton-X. The slides were developed in a DAB (3,3'-diaminobenzadine)-hydrogen peroxide solution (Vector Laboratories, Burlingame, Calif.). Controls included substitution of preimmune sera for primary antisera and antisera pre-adsorbed with excess antigen (100 $\mu$M GHRH-RP). Testicular sections were counterstained with cresyl violet. Hypothalamic sections were counterstained with methyl green.

EXAMPLE 2

Estimation of Size of Peptide

Western gel analysis was performed on crude tissue preparations of rate hypothalami and isolated testicular germ cells. Germ cells were isolated from six adult Sprague-Dawley rat testes using sequential collagenase and trypsin treatments as previously described [L. J. Romrell, A. R. Bellve, D. W. Fawcett, Dev. Biol., 49, 119 (1976)]. The isolated germ cells and five hypothalami from adult Sprague-Dawley rats were homogenized in the presence of antiproteases (50 $\mu$M pepstatin A, 30 KIU/ml aprotinin, 1 mM PMSF, 1 mM leupeptin and 1 mM iodoacetamide). These extracts were partially purified over Sep-Pak C18 columns (Waters, Milford, Mass.), eluted with 20%, 45% and 80% acetonitrile +0.1% trifluoroacetic acid and lyophilized. The tissue samples were analyzed by sodium dodecyl sulfate-polyacrylamide gel electrophoresis (SDS-PAGE) [U. K. Laemmli, Nature, 227, 681 (1970)], after boiling for 6 minutes in 2.3% SDS-10% glycerol, 62.5 mM Tris, 5% mercaptoethanol and 0.01% bromophenol blue adjusted with HCl to pH 6.8. Samples were separated on a 15% SDS polyacrylamide gel run overnight at 15 mA at room temperature and were transferred to Immobilon polyvinylidene difluoride membrane (0.45 $\mu$m pores; Millipore, Bedford, Mass.) for 90 minutes at 80 V in 25 mM Tris, 192 mM glycine, and 20% methanol, pH 8.3 at 4C. The standard used for SDS-PAGE was the low range protein molecular mass standards (Gibco BRL, Grand Island, N.Y.). The membrane was blocked for 1 hour in 50 mM Tris buffer, 105 mM NaCl, 0.% Tween, pH 7.5, containing 5% nonfat dried milk. The immunoreactions were performed at a 1:2000 dilution of the primary antisera overnight at 40C in Tris buffered saline pH 7.6, 0.1 Tween, 0.5% nonfat dried milk. Immunodetection by chemiluminescence was performed using the ECL Western blotting kit (Amersham, Arlington Heights, Ill.). Secondary goat antirabbit antisera was used at 1:1500 dilution. Signal specificity was evaluated by substitution of the primary antisera with antisera pre-adsorbed with excess antigen (50 µM GHRH-RP). The bands of interest (3.5 kDa and 10 kDa) were completely blocked using the pre-adsorbed antisera.

EXAMPLE 3

Activation of SCF in Sertoli Cells

Sprague-Dawley rats (20–22 day old) were obtained from Harlan Labs (Indianapolis, IN). All animals were maintained in accordance with the guidelines set by the Animal Use and Care Committee of I. U. School of Medicine (#A-3392-01). Sertoli cells were isolated using sequential collagenase and trypsin treatment and cultured using modifications of the method of Dorrington and Fritz [*Endocrinology* 94:879, 1975]. Sertoli cells were plated on 100 mm dishes and cultured at 32° C. in 10 ml of Ham's F12 media supplemented with 9 mM HEPES, pH 7.5, 215 µg/ml L-glutamine, 50 U/ml penicillin, 50 µg/ml streptomycin, 50 µg/ml gentamycin, and 0.625 µg/ml fungizone. Media was changed three days after plating and on day 4, Sertoli cells ($3 \times 10^6$/plate) were incubated with 10 and 100 nM rat GHRH-RP or rat GHRH as well as control media fro 16 hours. Cell purity was monitored by phase contrast microscopy and by comparative reverse transcription-polymerase chain reaction (RT-PCR) amplification. RT-PCR (25 cycles) was performed on the isolated Sertoli cell RNA using primer pairs for 3β-hydroxysteriod dehydrogenase and GHRH to evaluate for Leydig cell and germ cell contamination respectively [Monts et al., Peptides of the Growth Hormone-Releasing Hormone Family, *Endocrine* 4:1 pp. 73–78 (1996)]. The Sertoli cell RNA had no detectable contamination from these testicular cell types.

Sertoli cells were harvested by plate scraping and the RNA isolate by the guanidinium thiocyanate-phenol-chloroform extraction method [P. Chomczynski and N. Sacchi, Anal. Biochem. 162, 156 (1987)]. For Northern analysis, 10 µg of total RNA from each sample was electrophoresed on a 1.2% agarose gel containing 6.7% formaldehyde in MOPS buffer and then transferred and cross linked to a 0.45 µM MagnaGraph nylon membrane (MSI, Westboro, MA). The blots were hybridized to the following probes: murine SCF cDNA probe shown to cross-react with SCF (provided by David A. Williams, Indiana University), rat α-inhibin cDNA probe (provided by Kelly E. Mayo, Northwestern University), rat androgen binding protein (ABP) cDNA probe (provided by David R. Joseph, University of North Carolina), rat transferrin riboprobe (provided by Michael Griswold, Washington State University), and a human γ-actin CDNA probe which cross-hybridizes with rat actin (provided by Winston A. Salswer, UCLA) to control for RNA loading and transfer. cDNA probes were $^{32}$P-labeled by the hexanucleotide primer method using a kit from Stratagene (La Jolla, Calif.) and the blots were hybridized at 42° C. overnight. The transferrin riboprobe was $^{32}$P-labeled using a kit from Promega (Madison, WI) and the blots hybridized at 60° C. overnight. The blots were washed with 0.1×SSC and exposed to film at −80° C. Autoradiograms were scanned on a Microtek Scanmaker II, and data were quantified using Sigma Scan (Jandel Scientific, San Rafael, Calif.) using actin as control.

EXAMPLE 4

Mechanism of Action

Rat Sertoli cell cultures were prepared as described in Example 3 above. B. Bloch, A. Baird, N. Ling, R. Guillemin, *Endocrinology* 118, 156 (1986). On day 4 of culture, Sertoli cells were treated with GHRH-RP (100 nM), GHRH (100 nM), FSH (0.0275 U/ml) or vehicle for 30 minutes at 37° C. The cells were lysed in 0.05M glacial acetic acid, scraped off plates and then boiled and iced for 5 minutes. The resultant supernatant was assayed for cAMP using the Rianen $^{125}$I cAMP radioimmunoassay kit from Du Pont (Wilmington DE). Results were performed in triplicate and reproduced using several culture experiments.

EXAMPLE 5

Demonstration of Testis Exon 1

In this Example, it was demonstrated that GHRH mRNA found in testis includes an exon 1 sequence different from that in other tissues incuding the hypothalamus and placenta, and that the initation of GHRH transcription in testis begins approximately 700 bp 5' to that in placenta and approximately 10.7 kbp 5' to that in the hypothalamus. In addition, it has been found that regions of DNA just upstream of testicular exon 1 (and placenta exon 1) stimulate transcription in vitro in a rat germ cell nuclear extract, and thus these regions are expected to contain functional promoters.

Animals

Male Sprague-Dawley rats were obtained from Harlan (Indianapolis, Ind.). All animals were maintained in accordance with the guidelines set by the animal use and care committee of Indiana University School of Medicine.

Plasmids and Probes

Figure 3:
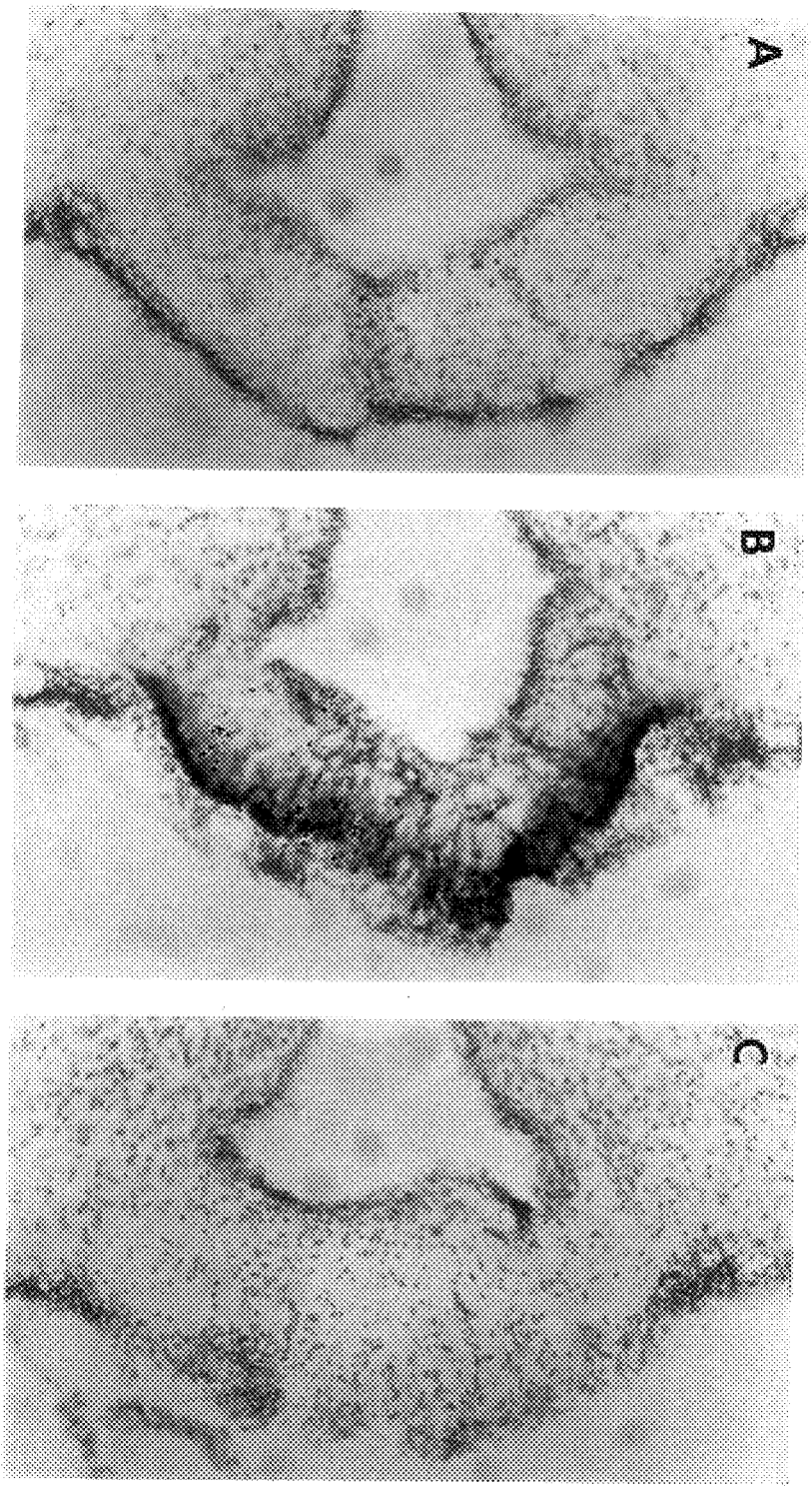
FIGS. 3 A–C are photomicrographs depicting the immunohistochemical localization of GHRH-RP in rat hypothalamus.

The plasmid prghrf-2, containing exon 3 through the polyadenylated [poly (A)$^+$] rat hypothalamic GHRH cDNA (Mayo, K. E., Cerelli, G. M., Lebo, R. V., Bruce, B. D., Rosenfeld, M. G., Evans, R. M. (1985) "Characterization of CDNA and Genomic Clones Encoding the Precursor to Rat Hypothalamic Growth Hormone-Releasing Factor", *Nature*, 314:464–467), was obtained from Dr. Ron Evans (Salk Institute, La Jolla, Calif.). an EcoRI-HindIII insert containing exons 3–5 was used as a probe. The plasmid EE5.0 containing 5 kilobases (kb) of GHRH genomic sequence was obtained from Dr. Kelly Mayo (Northwestern University, Evanston, IL). A 1.5-kb PvuII-BglII fragment extending from −500 basepairs (bp) relative to the hypothalamic transcription initiation site into hypothalamic intron A (Id.) was excised for use as a probe to screen the genomic library. The testicular exon 1 probe for the genomic Southern was a 307-bp PCR product extending from −200 relative to the initiation of transcription (FIG. 3) to the 3'end of testicular exon 1. The testicular exon 1 probe for the Northern blot was a 733-bp PCR product prepared from genomic DNA, extending from the 5'end of testicular exon 1 to the 3'end of placental exon 1. For hybridization, probes were labeled with 32P by the random primer method of Fineberg and Vogelstein (Feinberg, A. P., Vogelstein, B. (1983) "A Technique for Radiolabeling DNA Restriction Fragments to High Specific Activity", *Anal. Biochem.*, 132:6–13), using a Prim-It kit (Stratagene, La Jolla, Calif.).

Cell Fractionation and RNA Analysis

Germainal (spermatogenic) cells were isolated using sequential collagenase and trypsin treatment of adult testis, as described previously (Srivastava, C. H., Collard, M. W., Rothrock, J. K., Peredo, M. J., Berry, S. A., Pescovitz, O. H. (1993) "Germ Cell Localization of a Testicular GHRH-Like Factor", *Endocrinology,* 133:83–89; Mesitrich, M. L., Bruce, W. R., Clermont, Y. (1973) "Cellular Composition of Mouse Testis Cells Following Velocity Sedimentation Separation", *Exp. Cell. Res.,* 79:213–227; Romrell, L. J., Bellve, A. R., Fawcett, D. W. (1976) "Separation of Mouse Spermatogenic Cells by Sedimentation Velocity", *Dev. Biol.,* 49:119–131). RNA was extracted from germinal cells, total testis, and other tissues by the guanidinium thiocyanate-phenon-chloroform extraction method (Chomczynski, P., Sacchi, N. (1987) "Single Step Method of RNA Isolation by Acid Guanidinium Thiocyanate Extraction", *Anal. Biochem.,* 162:156–159). Poly(A)$^+$ RNA was isolated using oligo(deoxythymidine)-cellulose (Collaborative Research, Bedford, Mass). For Northern analysis, RNA was subjected to electrophoresis on a 1.5% formaldehyde-agarose gel in 3[N-morpholino]propanesulfonic acid buffer and transferred to a nylon membrane. Hybridization conditions were described previously (Srivastava, C. H., Breyer, P. R., Rothrock, J. K., Peredo, M. J., Pescovitz, O. H. (1993) "A New Target for Growth Hormone Releasing-Hormone Action in Rat: The Sertoli Cell", *Endocrinology,* 133:1478–1481; Srivastava, C. H., Rado, T., Bauerle, D., Broxmeyer, H. E. (1991) "Regulation of Human Bone Marrow Lactoferrin and Myeloperoxidase Gene Expression by Tumor Necrosis Factor-Alpha", *J. Immunol.,* 146:1014–1019).

Library Screening

A rat liver genomic library in a λ EMBL3 vector, purchased from Clontech (Palo Alto, Calif.), was screened with the GHRH probe described above. Two positive clones, clones 1 and 23, were purified and digested with XhoI. Fragments of 4 and 6 kb that mapped at the 5'ends of clones 23 and 1, respectively, were subcloned into the vector pGEM 7Z (Promega, Madison, Wis.).

A rat testicular cDNA library in a λ GT11 vector was purchased from Clontech and screened with the GHRH cDNA probe. One positive clone was detected and purified. The GHRH cDNA insert was removed by digestion with EcoRI and subcloned into PGEM 7Z for DNA sequencing using a Sequenase kit (U.S. Biochemical Corp., Cleveland, Ohio), [$^{35}$S]deoxy-ATP, and SP 6 and T7 primers (Sanger, F., Nicklen, S., Coulson, A. R. (1977) "DNA Sequencing with Chain-Terminating Inhibitors", *Proc. Natl. Acad. Sci. USA,* 74:5463–5467). Sequence analysis was performed using the University of Wisconsin Genetics Computer Group sequence analysis software (Devereux, J., Haeberli, P., Smithies, 0. (1984) "A Comprehensive Set of Sequence Analysis Programs for the VAX", *Nucleic Acids Res.,* 12:387–395).

RACE Protocol

All primers were provided by the Oligonucleotide Synthesis Facility, Wells Center for Pediatric Research, Indiana University School of Medicine (Indianapolis, Ind.).

For the 5'RACE, a kit from Gibco-BRL (Gaithersburg, Md.) was used. Germ cell poly(A)$^+$ RNA (1 μg) was used as a template for cDNA synthesis, with a GHRH exon 3-specific primer of the sequence 5'GGCTGTTCATGATTTCGTGCAGCAGTTTGC-3' (SEQ ID NO:10). The cDNA was C-tailed and amplified by PCR using a 5'primer the anchor primer supplied with the kit and a second nested exon 3 primer of the sequence 5'-ATATAATTGGCCCAGGATTCTCCGGTA-3' (SEQ ID NO:11). The reaction products were subjected to Southern blot analysis, using a ghrh exon 2 oligonucleotide probe. A second aliquot of each RACE product was electrophoresed on a 1.8% agarose gel, and a band of the size detected on the Southern blot was excised and purified using a Spin-X column (Costar, Cambridge, Mass.). The DNA fragment was cloned using the Clone-Amp system (Gibco-BRL), as previously described (Srivastava, C. H., Kelley, M. R., Monts, B. S., Wilson, T. M., Breyer, P. R., Pescovitz, O. H. (1994) "Growth Hormone-Releasing Hormone Receptor mRNA is Present in Rat Testis", *Endocr. J.,* 2:607–610; Kelley, M. R., Jurgens, J. K., Tentler, J., Emanuele, N. V., Blutt, S. E. Emanuele, M. A. (1993) "Coupled Reverse Transcription-Polymerase Chain Reaction (RT-PCR) Technique is Comparative, Quantitative, and Rapid:Uses in Alcohol Research Involving Low Abundance mRNA Species Such as Hypothalamic LHRH and GRF", *Alcohol,* 10:185–189). DNA from the resulting colonies was used for sequencing. Sequence obtained during the first round was sued to synthesize an oligonucleotide primer for a second RACE reaction.

The 3'RACE protocol was used to confirm the testicular GHRH mRNA sequence obtained from the cDNA clone. It was carried out as described by Frohman et al. (Frohman, M. A. (1990) "RACE:Rapid Amplification of cDNA Ends", In: Innis, M. A., Gelfand, D. H., Sninsky, J. J., White, J. J. (eds) *PCR Protocols: A Guide to Methods and Applications.* Academic Press, San Diego, pp 28–28; Frohman, M., Dush, M. K., Martin, G. R. (1988) "Rapid Production of Full-Length cDNAs from Rare Transcripts:Amplification Using a Single Gene-Specific oligonucleotide Primer", *Proc. Natl. Acad. Sci. USA,* 85:8998–9002), using the exon 3 primer 5' CATGCAGACGCCATCTTCACCAGC 3' (SEQ ID NO:12) for the 5' primer and the primer specified by Frohman (Frohman, M. A. (1990) "RACE:Rapid Amplification of cDNA Ends", In: Innis, M. A., Gelfand, D. H., Sninsky, J. J., White, J. J. (eds) *PCR Protocols: A Guide to Methods and Applications.* Academic Press, San Diego, pp 28–28) for the 3'primer in the PCR reaction.

RT-PCR Analysis

These procedures were performed as described previously (Srivastava, C. H., Kelley, M. R., Monts, B. S., Wilson, T. M., Breyer, P. R., Pescovitz, O. H. (1994) "Growth Hormone-Releasing Hormone Receptor mRNA is Present in Rat Tests", *Endocr. J.,* 2:607–610; Kelley, M. R., Jurgens, J. K., Tentler, J., Emanuele, N. V., Blutt, S. E., Emanuele, M. A. (1993) "Coupled Reverse Transcription-Polymerase Chain Reaction (RT-PCR) Technique is Comparative, Quantitative, and Rapid:Uses in Alcohol Research Involving Low Abundance mRNA Species Such as Hypothalamic LHRH and GRF", *Alcohol,* 10:185–189). Three micrograms of total RNA were mixed with 100 pmol oligo (deoxythymidine) primers (Promega) and H$_2$O, heated to 75 C for 10 min, and quenched on ice. Reverse transcriptase reaction buffer, placental ribonuclease inhibitor, and Superscript II reverse transcriptase (all from Gibco-BRL) were then added, and the reaction mix (in a final volume of 20 μl) was incubated at room temperature for 10 min and at 42 ° C. for 50 min. The reaction was terminated by heating at 95° C. for 5 min and quenching on ice. Ribonuclease-H (1 μl; Gibco-BRL) was then added to the reaction and incubated for 20 min at 37° C.

Five microliters of the reverse transcription reaction from each sample were subjected to PCR. The PCR was carried out using 35 cycles of amplification (94° C., 30 sec; 57° C., 45 sec; 72 ° C., 2 min), followed by 10 min at 72° C. After PCR, an aliquot of each reaction was electrophoresed on 1.8% agarose gels and transferred to nylon membranes. The blots were hybridized under conditions previously described (Srivastava, C. H., Kelley, M. R., Monts, B. S., Wilson, T. M., Breyer, P. R., Pescovitz, O. H. (1994) "Growth Hormone-Releasing Hormone Receptor mRNA is Present in Rat Testis", *Endocr. J.,* 2:607–610). The PCR products were cloned and sequenced as described above. The PCR primers were: testicular GHRH exon 1,5'ACGGAACATCGAGCCAAATCCA-3' (SEQ ID NO:13); placental GHRH exon 1,5'CTGGATCCCACAACTGCACA-3' (SEQ ID NO:14); hypothalamic GHRH exon 1,5'AGAGGGATACCTGTCACCTCA-'3 (SEQ ID NO:15); GHRH exon 2,5'-TGCCCCCCTCACCTCCCTTC-3' (SEQ ID NO:16); GHRH exon 4 (3'primer), 5'-GGCGGTTGAACCTGGATCTT-3' (SEQ ID NO:17) and testicular GHRH 5'flanking, 5'CATTGAGCTTATTGGAGCGTT-3' (SEQ ID NO:18).

For PCR reactions in which the products were sequenced, $(CAU)_4$ or $(CUA)_4$ was added to the 5'end of the primers for use with the Clone-Amp system (Gibco BRL, Grand Island, N.Y.).

Genomic Southern Blot

Rat liver DNA was isolated by standard protocols (Sambrook, J., Fritsch, E. F., Maniatis, T. (1989) *Molecular Cloning-A Laboratory Manual,* Ed 2, Cold Spring Harbor Laboratory, Cold Spring Harbor. Duplicate 10-μg aliquots were digested to completion with BamHI, EcoRI, or HindIII; subjected to electrophoresis on a 1% agarose gel; and transferred to a nylon membrane. The blots were hybridized to either a GHRH exon 3–5 probe or a testicular GHRH exon 1 probe.

The Genbank Accession numbers for the reported sequences in this Example are U10153, U10154, U10155, and U101056.

Results

To characterize the GHRH mRNA in testis, sequence analysis of a GHRH clone isolated from a testicular cDNA library was performed. The clone contained exons 2–5 of the mRNA, which were found to have a sequence identical to that of hypothalamic GHRH mRNA in the protein-coding region (FIG. 7A, SEQ ID NO:4)). Slight heterogeneity was seen in the 20 nucleotides immediately adjacent to the poly(A) sequence. This may result from polymorphism in the gene due to strain differences in the rats or to a cloning artifact. The putative peptide sequence is shown and is identical to the hypothalamic pre-pro-GHRH (Mayo, K. E., Cerelli, G. M., Rosenfeld, M. G., Evans, R. M. (1985) "Characterization of cDNA and Genomic Clones Encoding the Precursor to Rat Hypothalamic Growth Hormone-Releasing Factor", *Nature,* 314:464–467).

To determine the sequence of exon 1 of testicular GHRH mRNA, the 5'RACE protocol and, subsequently, RT-PCR, using testicular exon 1- and exon 4-specific primers, were employed. FIG. 7A (SEQ ID NO:4) shows the sequence of one testis-specific transcript. The exon 1 sequence is located approximately 700 by up-stream in the genome from that of placental exon 1. FIG. 7, B (SEQ ID NO:6) and C (SEQ ID NO:7), depict two alternative transcripts. FIG. 7B (SEQ ID NO:6) shows a transcript containing part of placental exon 1 (Gonzales-Crespo, S., Boronat, A. (1991) "Expression of the Rat Growth Hormone-Releasing Hormone Gene in Placenta is Directed by an Alternative Promoter", *Proc. Natl. Acad. Sci. USA,* 88:8749–53) (labeled testis exon 1A) spliced between testicular exon 1 and exon 2. FIG. 7C (SEQ ID NO:7) shows a transcript containing a 740-nucleotide exon 1 extending from the 5'end of testicular exon 1 through testicular exon 1A (placental exon 1) and containing all of the intervening genomic sequence. The sequences of exons 2–4 of these transcripts were identical to those of hypothalamic GHRH mRNA. The data demonstrate that multiple GHRH transcripts exist in testis, and that they arise from alternative splicing between exons 1 and 2.

Figure 8:
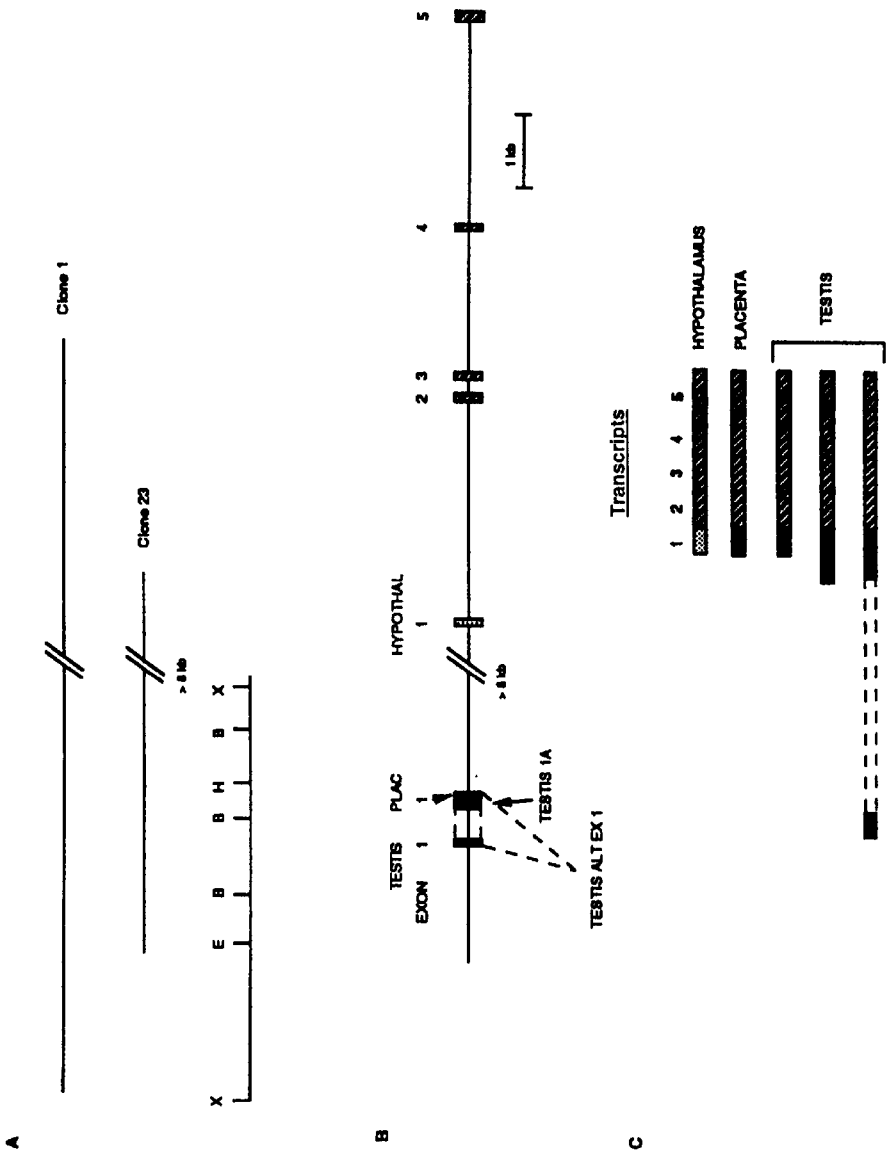
FIGS. 8A–C show a diagram of the rat GHRH gene.

Based on these and previously reported data (Mayo, K. E., Cerelli, G. M., Rosenfeld, M. G., Evans, R. M. (1985) "Characterization of cDNA and Genomic Clones Encoding the Precursor to Rat Hypothalamic Growth Hormone-Releasing Factor", *Nature,* 314:464–467; Gonzalez-Crespo, S., Boronat, A. (1991) "Expression of the Rat Growth Hormone-Releasing Hormone Gene in Placenta is Directed by an Alternative Promoter", *Proc. Natl. Acad. Sci. USA,* 88:749–53), we predicted the structure of the rat GHRH gene (FIG. 8, B and C). One placental GHRH exon 1 is shown; several potential sites for initiation of GHRH transcription in placenta had previously been found (Id.). In the model shown in FIG. 8, B and C, testicular transcription begins approximately 700 bp 5' to transcription initiation in the placenta and more than 10.7 kbp 5' to that in hypothalamus. We found at least three transcripts in testis; these result from alternative splicing. Based on the sequence of these, some testicular GHRH transcripts contain six exons.

We next defined the site of initiation of transcription of the GHRH gene in the testes. A genomic probe extending from −500 bp relative to the hypothalamic transcription initiation site through hypothalamic intron A was used to isolate clones from a rat genomic library. Two clones, clones 1 and 23, were purified and characterized (FIG. 8A). Clone 1 extends 3000 bp up-stream of testicular exon 1, and clone 23 extends 1000 bp up-stream of testicular exon 1, and clone 23 extends 1000 bp up-stream of testicular exon 1. The genomic clones were sequenced to approximately −660 bp relative to the initiation of transcription detected by RACE analysis. Computer analysis showed a TAT-like sequence at −60 bp and several cis-acting elements in the promoters of genes expressed in testis (Kilpatrick, D. K., Zinn, S. A., Fitzgerald, M., Higuchi, H., Sabol, S. L., Meyerhardt, J. (1990) "Transcription of the Rat and Mouse Proenkephalin Genes is Initiated at Distinct Sites in Spermatogenic and Somatic Cells", *Mol. Cell. Biol.,* 10:3717–3726; van der Hoorn, F. A. (1991) "Identification of the Testis C-Mos Promoter:Specific Activity in a Seminiferous Tubule-Derived Extract and Binding of a Testis-Specific Nuclear Factor", *Oncogene,* 7:1093–1097) (FIG. 9, SEQ ID NO:8). Three potential transcription initiation sites were determined by 5'RACE and by RT-PCR (FIG. 9, SEQ ID NO:10). Repeated RACE using testicular exon 1 oligonucleotide as the 3'PCR primer did not reveal any further sequence at the 5'-end of the testicular GHRH mRNA.

To confirm the presence of GHRH mRNA containing testicular exon 1 and the alternative first exons in testis, Northern blot analysis was performed on poly(A)$^+$ RNA from whole testis or germ cells, using either a genomic DNA probe extending from testicular exon 1 through placental exon 1 or a cDNA exon 3–5 probe. As shown in FIG. 10, the genomic probe (FIG. 10A) hybridized to RNA from both germ cells and placenta (FIG. 10B, left panel) as well as RNA from whole testis (FIG. 10B, right panel). At least two species of hybridizing RNA were seen, one similar in size to the 750-nucleotide transcript found in placenta and hypothalamus (Mayo, K. E., Cerelli, G. M., Rosenfeld, M. G., Evans, R. M. (1985) "Characterization of cDNA and Genomic Clones Encoding the Precursor to Rat Hypothalamic Growth Hormone-Releasing Factor", *Nature,* 314:464–467; Frohman, M. A., Downs, T. R., Chomczynski, P., Frohman, L. A. (1989) "Cloning and Characterization of Mouse Growth Hormone-Releasing Hormone (GRH)

Complementary DNA:Increased GHR Messenger RNA Levels in the Growth Hormone-Deficient Lit/Lit Mouse", *Mol. Endocrinol.,* 3:1529–1536; Gonzalez-Crespo, S., Boronat, A. (1991) "Expression of the Rat Growth Hormone-Releasing Hormone Gene in Placenta is Directed by an Alternative Promoter", *Proc. Natl. Sci. USA,* 88:8749–53) and, in addition, a larger species of 1.5–1.7 kb, as had been seen previously (Berry, S. A., Pescovitz, O. H. (1988) "Identification of a GHRH-Like Substance and its Messenger RNA in Rat Testis", *Endocrinology,* 123:661–663; Bagnato, A., Moretti, C., Ohnishi, J., Frajese, G., Catt, K. J. (1992) "Expression of the Growth Hormone-Releasing Hormone Gene and its Peptide Product in the Rat Ovary", *Endocrinology,* 130:1097–1102). The same species of RNA were detected with a GHRH exon 3–5 probe (FIG. 10B, right panel).

It is possible that the alternative GHRH transcripts found in testis result from a second GHRH gene. This is not likely, as there is only one copy of the human GHRH gene, located on chromosome 20 (Mayo, K. E., Cerelli, G. M., Lebo, R. V., Bruce, B. D., Rosenfeld, M. G., Evans, R. M. (1985) "Gene Encoding Human Growth Hormone-Releasing Factor Precursor:Structure, Sequence and Chromosome Assignment", *Proc. Natl. Acad. Sci. USA,* 82:63–67). However, to test this possibility, we performed a Southern blot analysis of BamHI-, EcoRI-, and HindIII-digested rat liver genomic DNA, using a GHRH exon 3–5 probe. We detected only the bands seen by Mayo et al. (Mayo, K. E., Cerelli, G. M., Rosenfeld, M. G., Evans, R. M. (1985) "Characterization of cDNA and Genomic Clones Encoding the Precursor to Rat Hypothalamic Growth Hormone-Releasing Factor", *Nature,* 314:464–467) in their genomic clones, suggesting that there is only one copy of the GHRH gene in the rat (FIG. 11, right panel). This is confirmed by the finding that the testicular exon 1 probe hybridized to only one restriction fragment in each lane (FIG. 11, left panel). The restriction fragments detected by this probe are identical to those of the genomic clones isolated by us from a library and to those previously detected with a placental cDNA probe (Gonzales-Crespo, S., Boronat, A. (1991) "Expression of the Rat Growth Hormone-Releasing Hormone Gene in Placenta is Directed by an Alternative Promoter", *Proc. Natl. Acad. Sci. USA,* 88:8749–53).

To determine whether transcripts containing hypothalamic exon 1 are present in testis or whether transcripts containing testicular exon 1 are present in hypothalamus, RT-PCR using testicular or hypothalamic exon 1 primers and the exon 4 primer on germ cell or hypothalamic RNA was performed. Liver RNA was included as a negative control. FIG. 12 shows a Southern blot of the PCR products hybridized to the GHRH exon 3–5 probe. As shown in the top panel, several products were detected in the germ cell RNA with the testicular exon 1 primer, as previously noted, but none was seen in the hypothalamic RNA. Conversely, with the hypothalamic exon 1 primer, a product was detected only in the hypothalamus. PCR with the exon 2–4 primers resulted in products in both testis and hypothalamus, in agreement with the sequence data. No product was detected in liver with any of the primers. These data do not exclude the possibility that these transcripts are expressed at low levels not detected by our methods.

EXAMPLE 6

Figure 13:
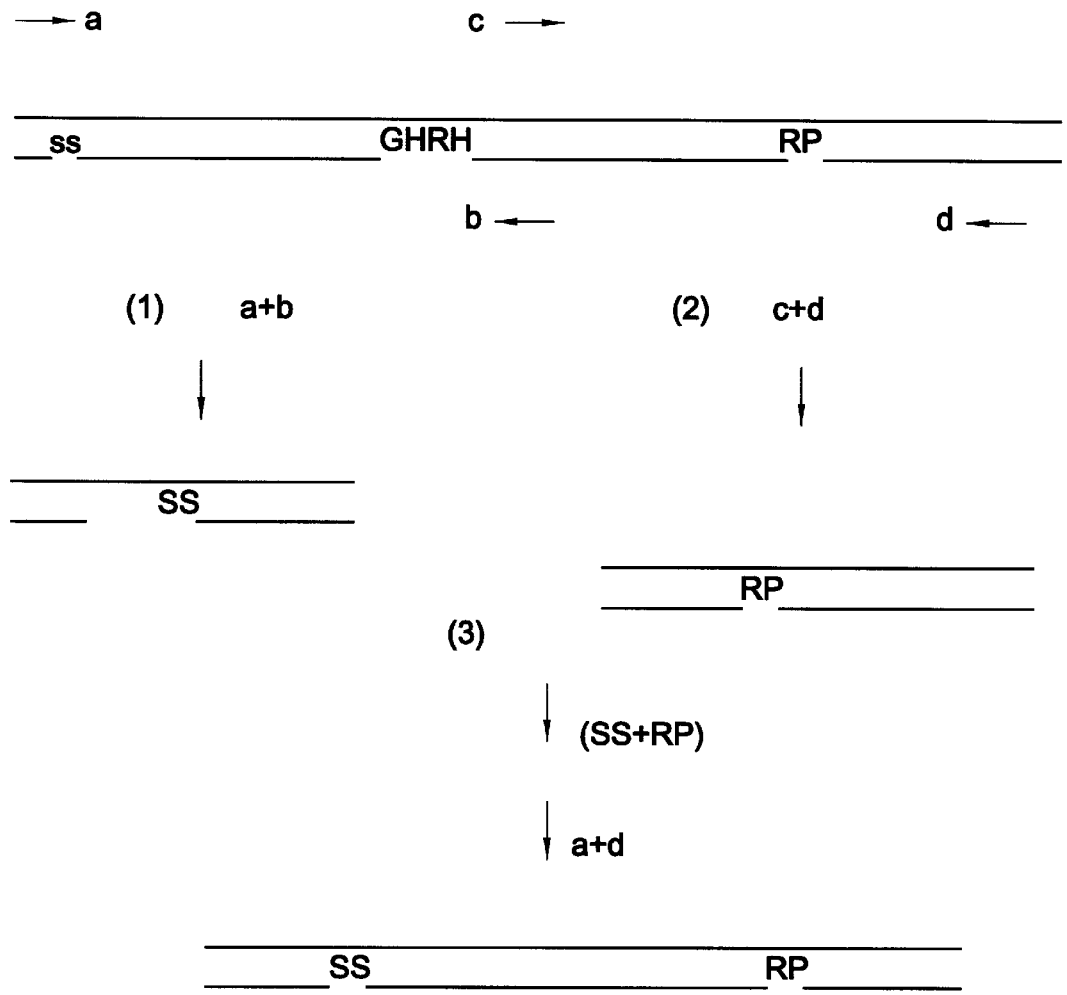
FIG. 13 is a schematic diagram showing SS (primers: a and b) and RP (primers: c and d) fragment as generated by PCR amplification, as described in Example 7. SS-RP is generated by the overlay extension method using a and d primers.

Recombinant Expression of GHRH-RP Polypeptide
6.1 Construction of SS-RP and SS-RP Expression A. Generation of Signal-Sequence/RP cDNA by PCR Amplification Plasmid PGEM-4 (2,871 bp) containing a 634 bp mouse GRF-E2 cDNA (from Mayo laboratory) was used as a template in PCR amplification reactions. SS and RP cDNAs were generated using the following reaction conditions: DNA templates (1 μpg) were added to a 50 μl total volume solution containing 2×PCR buffer (10 mM Tris-HCl PH 8.3, 50 mM KC1, 2.5 mM MgCl2, 0.0% gelatin), and 200 μM of dNTP. To the mixture, added to 50 pmol of each of two synthetic oligonucleotides were added: Primer R1-SS-a (5'AGACGAATTCATGCTGCTC TGGGTGCTC-3,) (SEQ ID NO:19) contains a recognition sequence for EcoRI and a sequence of 10 nt complementary SS at 5' end. Primary WQ-RP-b (5'-GGGAAGTCCTACGTCG-CTGTCCTTCTGTCGTACACC-3') (SEQ ID NO:20) and primer PR-QW-c (5'CCCTTCAGGATGCAGCGACAGGAAGACAGCAT-GTGG-3') (SEQ ID NO:2) have 18 nt complementary to the 3' end of SS DNA sequence and 18 nt complementary to the 5' end of RP DNA sequence. Primer Stop-SalI-d (5'TTCGGAAGTCGCCTGCGAACTCAGCTGCAGA-3') (SEQ ID NO:22) is complementary to the 3' end of RP DNA sequence and also contains 13 nt which encode a stop codon and a SalI restriction site (FIG. 13). TFL DNA polymerase (Pharmacia LKB) was added to the PCR reaction and DNA amplification was performed for 30 cycles in DNA thermal cycler (conditions: denaturation at 95° C. for 30 s, annealing at 60° C. for 60 s, and extension at 72° C. for 2 min for each cycle). After amplification, 50 μl of each PCR reaction mixture were fractionated by electrophoresis (80 V, 2h) along with a molecular weight marker in a 1.8% low melting agarose gel to confirm the size of the amplification products. Primers R1-SS-a and WQ-RP-b amplify a 100 bp cDNA sequence which encode a SS and an EcoRI restriction site. Primers PR-WQ-c and Stop-SalI-d amplify a 103 bp cDNA sequence which encodes a RP and stop codon and a SalI restriction site. Each PCR-amplified DNA fragment was excised from the low melt agarose gel and purified (QIAEX for DNA Extractin from Agarose Gels. QIAGEN, Inc.).

SS-RP cDNA was generated using the PCR overlap extension technique. The first PCR-generated, purified cDNA SS and RP fragments (100 ng) were used in the second PCR overlap extension reaction. Aliquots from two separate PCR reactions containing the overlapping fragments were mixed and subjected to PCR amplification using primers SS-R1-a and Stop-SalI-d. They amplify a 168 bp SS-RP cDNA sequence. The reaction was performed for 20 cycles in DNA thermal cycler (conditions: denaturation at 95° C. for 30 s, annealing at 55° C. for 30 s, and extension at 72° C. for 45 s for each cycle). After amplification, 50 μl of each PCR reaction product was fractionated b electrophoresis (80 V, 2h) along with a molecular weight marker in a 1.8% low melting agarose gel to confirm the size of the amplification products. The PCR-amplified DNA fragment was excised from the low melt agarose gel and purified (QIAEX for DNA Extraction from Agarose Gels. QIAGEN, Inc.) and used for subcloning.

B. Subcloning of SS-RP cDNA into PCI Vectors

Twenty μg of PCR product (SS-RP) and the 3.7 Kb pCI vector (10 μg) were digested separately with EcoRI and SalI (1U/μg, 37° C., 3h). Then PCI vector was dephosphorylated with calf intestinal alkaline phosphatase at 37° C. for 30 min. The digested SS-RP product and the dephosphorylated pCI vector were fractioned by electrophoresis in 1.8% low melt agarose gel at 80V for 3h and excised from agarose gel, purified (QIAEX for DNA Extraction from Agarose Gels, QUAGEN, Inc.) and ligated (16° C., overnight, 1 Unit T4 DNA ligase, 3:1 molar ratio of fragment:vector DNA). 1 μl of the ligation reaction was used to transform 20 μl competent E. coli HB 101 cells. Transformed HB 101 cells were plated onto LB agar plates containing 100 μg/ml ampicillin and incubated at 37° C. for 16h. Bacterial colonies were randomly chosen from each plate, grown in culture (3 ml LB broth, 100 μg/ml ampicillin, 37° C. overnight) and used for plasmid DNA isolation (QIAGEN, Inc.). The identity of the subcloned DNA was confirmed by digestion of the plasmid DNA (1 μg) with EcoRI and SalI (10U/μg, 37° C., 2h) and two bands were identified. DNA sequencing was performed of the products to verify the insert SS-RP was correct sequencing.

6.3 Results: Construction of SS-RP cDNA and Subcloning Into Vector PCI.

Figure 14:
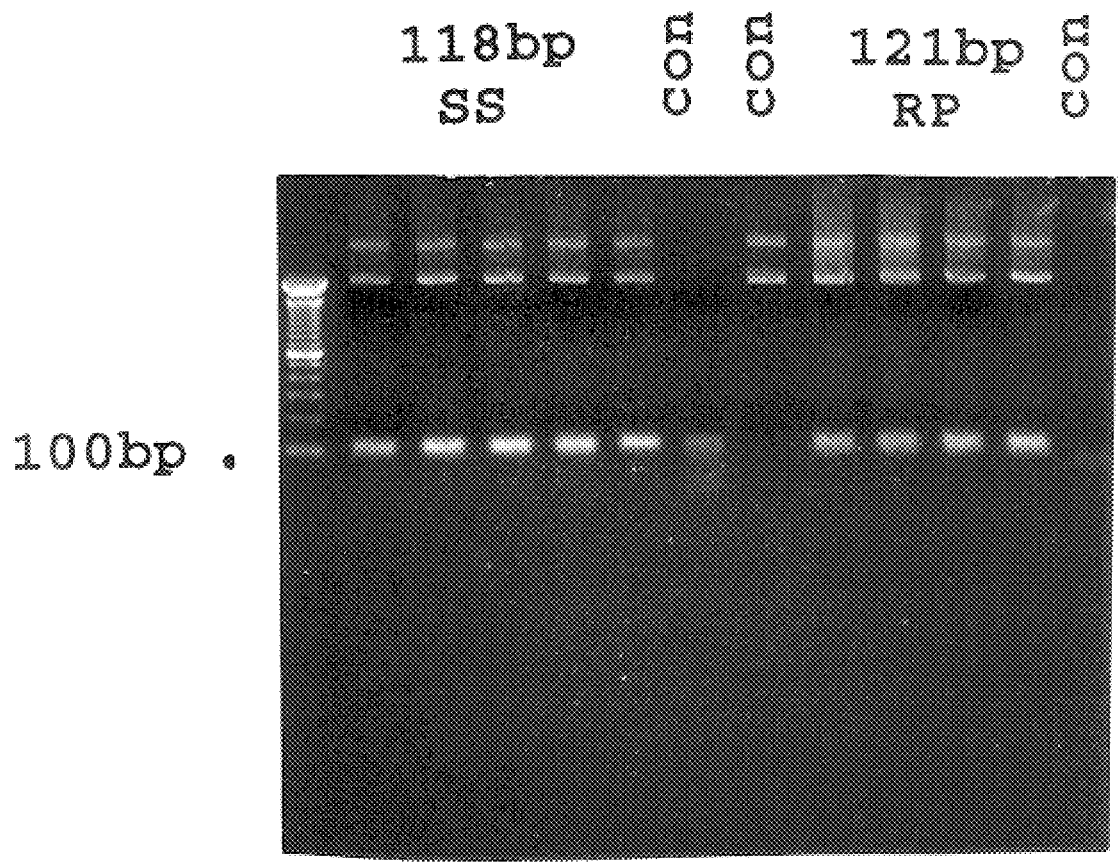
FIG. 14 is shows PCR amplification of control and SS and RP cDNAs. These PCR products wre analyzed by electrophoresis on an ethidium bromide-containing 2.0% agarose gel and photographed. Sizes of 100 bp ladder are also indicated. The product sizes are: SS (118 bp); RP (121 bp).
Figure 15:
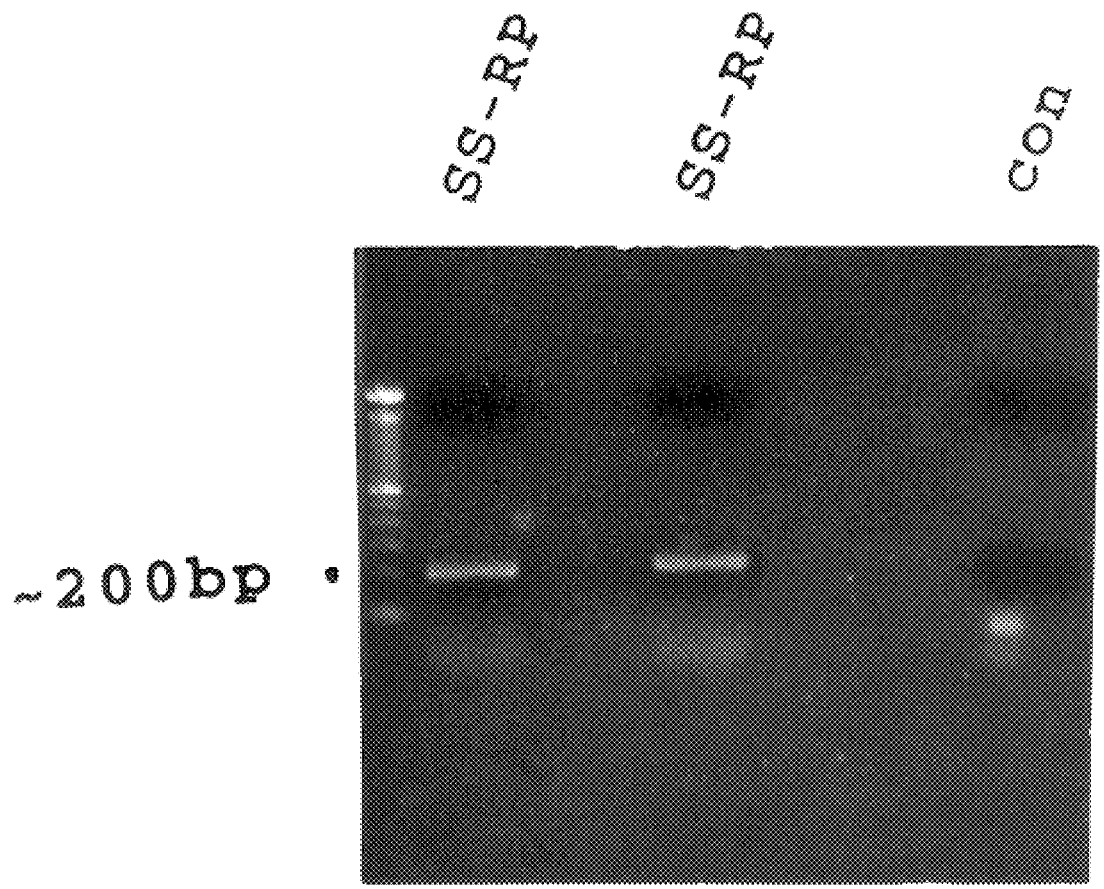
FIG. 15 shows second PCR amplification of control and SS-RP cDNA as described in Example 6. The PCR products were analyzed by electrophoresis on an ethidium bromide-containing 2.0% agarose gel and photographed. Sizes of 100 bp ladder are also indicated.
Figure 16:
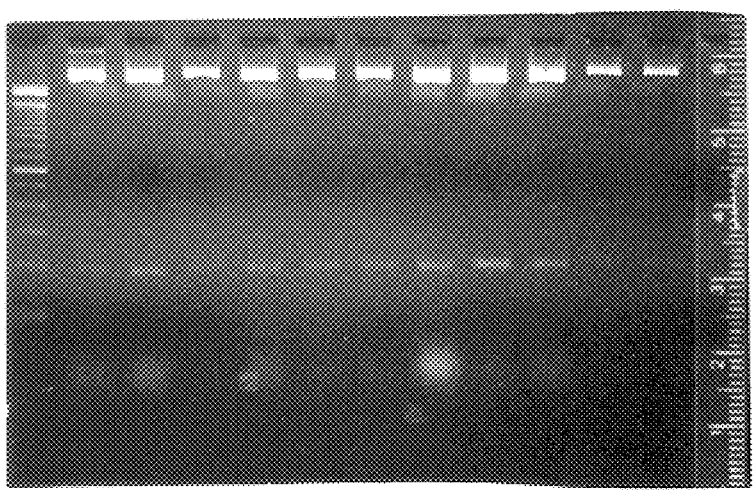
FIG. 16 shows the confirmation of the identity of subcloned DNA by plasmid DNA digestion with EcoRI and SalI, as described in Example 6. The digestions were analyzed on an ethidium bromide-containing 2.0% agarose gel and photographed. The sizes of the DNA SS-RP was as predicted (203 bp). Sizes of 100 bp ladder are indicated.

SS and RP were synthesized by PCR and the products were of the correct predicted size by agarose gel electrophoresis using molecular weight markers (shown in FIG. 14). Following the second PCR amplification, the SS-RP product was made and the size of the product was confirmed by agarose gel electrophoresis (FIG. 15). The SS-RP cDNA fragment was digested with EcoRI and SalI and ligated into a pCI vector that had previously been digested with EcoRI and SalI and the ligated mixture was used to transform E. coli stain HB 101. The size of the subcloned DNA was confirmed by plasmid DNA digestion with EcoRI and SalI (FIG. 16). The insert contained the correct sequencing as confirmed by direct sequencing (FIG. 17, SEQ ID NO:9). NIH 3T3 and TM4 cells are transfected with the SS-RP gene construct and cultured to produce the encoded recombinant SS-RP protein.

EXAMPLE 7

Transgenic Mammals 7.1. Transgenic Mice With the GHRH-RP Gene

Using overlapping thermocycle amplification and fusion technology, the mouse GHRH signal sequence has been fused onto the GHRH-RP portion of the GHRH gene (See generally FIG. 18). This fusion retains the protease cleavage site following the amino acids QR of the signal sequence allowing for protease cleavage to occur following the signal sequence and the GHRH-RP portion resulting in the RP portion to be released from the signal sequence domain. The sequence of the SS-RP fusion protein is MLLWVLFVIL-ILTSGSHCSLPPSPPFRMQRQEDSMWT-EDKWMTLESILQGFPRMKPSADA (SEQ ID NO:23). This construction removes the GHRH portion from the configuration. The fused gene was cloned into the EcoRI and SalI sites in the modified pCI vector from Promega. In the modified plasmid, pPGKCI, we have replaced the CMV promoter with the murine PGK promoter. The functional splicing signals and SV40 poly A sequences contained in the pCI plasmid are maintained. The CMV promoter and enhancer have been replaced by mouse PGK which is expressed in all mice tissues. This construct was sequenced to confirm correct DNA authenticity and the plasmid used in transient transfection assays to determine the expression of the "fused" SS-RP construct. Plasmid DNA is injected into pronuclei of C3H/HeJ mice as previously described. Transgenic mice derived from these injections are first analyzed for the presence and expression of the transgene by Southern blots of tail DNA and RNA analysis of a wide variety of tissues. The transgenic mice protocol utilizes standard pronuclear-injection derived transgenic mice.

7.2 Knock-out of the GHRH-RP Domain of the GHRH Gene

Two different gene disruption strategies are employed, as generally described in Bronson, S. K. and Smithies, O., "Altering mice by homologous recombination using embryonic stem cells", *J. Biol. Chem.* 269: 27155–27158 (1994). The first involves a direct gene replacement with three stop codons inserted immediately following the GHRH domain of the amino terminal portion of sites in the GHRH gene such that the expression of the GHRH gene will be terminated immediately following the GHRH domain of this gene and elimination of the GHRH-RP peptide will be accomplished. This involves one distinct homologous recombination step in ES cells. The gene is disrupted using a targeting vector consisting of 5' and 3' flanking regions of the GHRH gene encompassing genomic domains upstream and downstream of the RP region. The neomycin (neo) gene will be included in this configuration such that it is inserted downstream of the last exon (exon 5) and should not cause any deleterious effect on the GHRH gene expression. After transfection, cells that have undergone recombination are selected for resistance to G418. Usually the selected cells are not homozygous so analysis of the resulting chimeric mice are not as informative. Therefore, homozygous ES cells with the gene altered will be selected for in one of two ways, either a hygromycin vector, constructed in exactly the same manner as the neo resistant construct is used to disrupt the second allele, or ES cells are selected using increasing concentrations of G418 usually resulting in clones that have two copies of the neo gene due to the mutation becoming homozygous.

The second technique involves the use of the loxP-cre system, such that loxP sites are inserted at the 5' and 3' ends of the replacement fragment and encompassing the fifth exon such that when combined with the recombinase cre, through matings with mice that contain the cre recombinse, the region between the loxP sites is recombined out of the genomic DNA and a single loxP site remains. This results, in this particular instance, in the deletion of most of the RP region and a non-functional RP peptide that maintains the protease cleavage site between the GHRH and GHRH-RP domain allowing for the short, non-functional RP protein to be processed from the total precursor protein. The advantage of this second procedure results in the advantage of removing the neo gene from the mice, in vivo, but, more importantly, the ability to mate the mice containing the loxP construct with mice containing the cre recombinase. This latter fact is advantageous as a large number of mice strains have been and are being created with the cre recombinase expressed in a tissue specific manner, allowing for the disruption of the RP protein to be accomplished in designated tissues only (Jackson Labs).

Alternatively, other constructs will be, or could be created that perform the same function, i.e., disruption of the carboxy terminal region of the GHRH gene such that the GHRH-RP portion of this gene is not expressed resulting in a "knock-out" or complete loss of the production of a functional GHRH-RP peptide, but maintaining the amino terminal portion of the gene, namely the GHRH peptide and associated signal sequence for protein processing.

Several clones with homologous recombination are then used in standard blastocyst injection to create the mice which are maintained and analyzed in standard fashion. Injections for both knock-out and transgenic mice are accomplished as generally described in Manipulating the Mouse Embryo, A Laboratory Manual, Brigid Hogan, et al., Cold Spring Harbor Laboratory (1986).

All references cited herein are indicative of the skills possessed by one ordinarily skilled in the art, and all such references are hereby incorporated herein by reference as if each had been individually incorporated by reference and fully set forth.

What is claimed is:

1. A method for stimulating the production of stem cell factor by Sertoli cells, comprising contacting the cells with an effective amount of GHRH-RP to stimulate the production of stem cell factor by the cells.

2. The method of claim 1, wherein the GHRH-RP is selected from:

(a) a polypeptide having the sequence of a native GHRH-RP polypeptide; and (b) a polypeptide which is at least 80% similar to a polypeptide of (a), as determined by the GAP program, and which stimulates the production of stem cell factor in Sertoli cells.

3. The method of claim 2 wherein the GHRH-RP is human GHRH-RP.

4. The method of claim 2 wherein the GHRH-RP is rat GHRH-RP.

5. A method for stimulating spermatogenesis in a mammal in need thereof, comprising contacting Sertoli cells of the mammal with a therapeutic amount of GHRH-RP to stimulate spermatogenesis in the mammal.

6. The method of claim 5, wherein the GHRH-RP is selected from:

(a) a polypeptide having the sequence of a native GHRH-RP; and
(b) a polypeptide which is at least 80% similar to a polypeptide of (a), as determined by the GAP program, and which stimulates the production of stem cell factor in Sertoli cells.

7. The method of claim 6 wherein the GHRH-RP is human GHRH-RP.

8. The method of claim 6 wherein the GHRH-RP is rat GHRH-RP.

* * * * *

SEQUENCE LISTING

<160> NUMBER OF SEQ ID NOS: 23

<210> SEQ ID NO 1
<211> LENGTH: 31
<212> TYPE: PRT
<213> ORGANISM: Homo sapiens

<400> SEQUENCE: 1

Gln Val Asp Ser Met Trp Ala Glu Gln Lys Gln Met Glu Leu Glu Ser
 1               5                  10                  15

Ile Leu Val Ala Leu Leu Gln Lys His Ser Arg Asn Ser Gln Gly
            20                  25                  30

<210> SEQ ID NO 2
<211> LENGTH: 30
<212> TYPE: PRT
<213> ORGANISM: Mus musculus

<400> SEQUENCE: 2

Gln Glu Asp Ser Met Trp Thr Glu Asp Lys Gln Met Thr Leu Glu Ser
 1               5                  10                  15

Ile Leu Gln Gly Phe Pro Arg Met Lys Pro Ser Ala Asp Ala
            20                  25                  30

<210> SEQ ID NO 3
<211> LENGTH: 30
<212> TYPE: PRT
<213> ORGANISM: Rattus norvegicus

<400> SEQUENCE: 3

His Leu Asp Arg Val Trp Ala Glu Asp Lys Gln Met Ala Leu Glu Ser
 1               5                  10                  15

Ile Leu Gln Gly Phe Pro Arg Met Lys Leu Ser Ala Glu Ala
            20                  25                  30

<210> SEQ ID NO 4
<211> LENGTH: 526
<212> TYPE: DNA
<213> ORGANISM: Rattus norvegicus
<220> FEATURE:
<221> NAME/KEY: CDS
<222> LOCATION: (98)..(409)

<400> SEQUENCE: 4
ctgcggatgc cacggaacat cgagccaaat cccaggaaca cgctctgaac cccaggagct      60
gcacaccact ctattaggtc ccgcccagga gtgaagg atg cca ctc tgg gtg ttc     115
                                       Met Pro Leu Trp Val Phe
                                         1               5 ttt gtg ctc ctc acc ctc acc agt ggc tcc cac tgc tca ctg ccc ccc      163
Phe Val Leu Leu Thr Leu Thr Ser Gly Ser His Cys Ser Leu Pro Pro
            10                  15                  20 tca cct ccc ttc agg gtg cgg cgg cat gca gac gcc atc ttc acc agc      211
Ser Pro Pro Phe Arg Val Arg Arg His Ala Asp Ala Ile Phe Thr Ser
        25                  30                  35 agc tac cgg aga atc ctg ggc caa tta tat gcc cgc aaa ctg ctg cac      259
Ser Tyr Arg Arg Ile Leu Gly Gln Leu Tyr Ala Arg Lys Leu Leu His
    40                  45                  50 gaa atc atg aac agg cag caa ggg gag agg aac cag gaa caa aga tcc      307
Glu Ile Met Asn Arg Gln Gln Gly Glu Arg Asn Gln Glu Gln Arg Ser
55                  60                  65                  70

```
agg ttc aac cgc cat ttg gac aga gtg tgg gca gag gac aag cag atg      355
Arg Phe Asn Arg His Leu Asp Arg Val Trp Ala Glu Asp Lys Gln Met
             75                  80                  85 gcc ctg gag agc atc ttg cag gga ttc cca agg atg aag ctt tca gcg      403
Ala Leu Glu Ser Ile Leu Gln Gly Phe Pro Arg Met Lys Leu Ser Ala
     90                  95                 100 gag gct tgagccctcg gccccaaac atagctggac cctgttactt ctacttcagt        459
Glu Ala tctgatcttc tccttcctct gtgaatacaa taaagaccca gttctcatct gcaaaaaaa     519 aaaaaaa                                                              526

<210> SEQ ID NO 5
<211> LENGTH: 104
<212> TYPE: PRT
<213> ORGANISM: Rattus norvegicus

<400> SEQUENCE: 5

Met Pro Leu Trp Val Phe Phe Val Leu Leu Thr Leu Thr Ser Gly Ser
 1               5                  10                  15

His Cys Ser Leu Pro Pro Ser Pro Pro Phe Arg Val Arg Arg His Ala
             20                  25                  30

Asp Ala Ile Phe Thr Ser Ser Tyr Arg Arg Ile Leu Gly Gln Leu Tyr
         35                  40                  45

Ala Arg Lys Leu Leu His Glu Ile Met Asn Arg Gln Gln Gly Glu Arg
     50                  55                  60

Asn Gln Glu Gln Arg Ser Arg Phe Asn Arg His Leu Asp Arg Val Trp
 65                  70                  75                  80

Ala Glu Asp Lys Gln Met Ala Leu Glu Ser Ile Leu Gln Gly Phe Pro
                 85                  90                  95

Arg Met Lys Leu Ser Ala Glu Ala
                100

<210> SEQ ID NO 6
<211> LENGTH: 253
<212> TYPE: DNA
<213> ORGANISM: Rattus norvegicus

<400> SEQUENCE: 6
ctgcggatgc cacggaacat cgagccaaat cccaggaaca cgctctgaac cccaggagct     60
gcacaccact ctattaggcc caggacggag aaggaggcgt cctgctcctg ccagccttaa    120
gatgggaatt ttagggtctg gacatcactg gtgctccagg tcagctttcc tggttgcaga   180
tctctcctgg tcaaggctcc cagctcgcct ggatcccaca actgcacagt gtcccgccca   240
ggagtgaagg atg                                                      253

<210> SEQ ID NO 7
<211> LENGTH: 771
<212> TYPE: DNA
<213> ORGANISM: Rattus norvegicus

<400> SEQUENCE: 7
ctgcggatgc cacggaacat cgagccaaat cccaggaaca cgctctgaac cccaggagct     60
gcacaccact ctattaggta gtttattggc gcatcaaatc tggagtctac ctccctcggt   120
tcacaaatca gttcagagag aggatcaaac ttgcccaaga ttaaagagta atggtgtcac   180
ctgctcctct tccctgaatg gcatgatgcc agggatgtga ctggtgacct gaagggagg    240 gaaatcaagg caggaacggc tgggtgtgat ggagacctca aggctgttgt gagcccccca   300
```

```
agaacagact ctctggaggc aggctttatc gagcaggtcg ttcaactggg gagcacaaag      360
gctacttaaa ttttggggga gtgagtaggg gcactcaggg caaacggatg tcattgtcca      420
agaccaaggt gtagggaatg ctttactgca tgaaaaggaa tttgaggtgc ttgctgtctg      480
gacgtgactt tgtccagaga ggaaattta  cctataacct ggccaccggt tatgactacc      540
tcaaggattg cagaggtggg gccaaaaggc tatgtacgtg ctctggaaca tgcaggccca      600
ggacggagaa ggaggcgtcc tgctcctgcc agccttaaga tgggaatttt agggtctgga      660
catcactggt gctccaggtc agctttcctg gttgcagatc tctcctggtc aaggctccca      720
gctcgcctgg atcccacaac tgcacagtgt cccgcccagg agtgaaggat g               771

<210> SEQ ID NO 8
<211> LENGTH: 737
<212> TYPE: DNA
<213> ORGANISM: Rattus norvegicus

<400> SEQUENCE: 8
gaactgcctt cctggatgag gactgcatga gcagagacct ggtgatggga gcccactaag       60
gcctgccgga ggagctagaa gtagaagcag gaaccactgg agctgagtct cctctctcca      120
gatgccacag cctgtcagaa gcgggactcg ggaaaagggc ttctcttccg ccccaggaca      180
gagtctgttt tgtttctcgc ctactctgtc tggctcctct ccaacaccag ttcttaaggc      240
tctggacata cacaattcca caggcccctc tcccaggatc cagaaacagg acagtcacat      300
ccggcatcct ctgccaaccc cggctcctcc agcttcatcg cagtcctcag tccctggcaa      360
ccacccaccg aatccccttc cctgccaccg tgtgtggaag cgggatactg gacagtcatt      420
ttagctgatt tgttcaattt gtttcctgag cttttgggcaa cccactccat ctgtagatgg      480
ctgtaagcaa cttccaagca gcatgccttc ctagccacct cccaggagct ccccaagggc      540
tgcctttcat tctccttcca ggggtctgta gaatacagcc ctggatgttt ccaaggcacg      600
gactggcata ataagcgcag gcgtctccat gacaccgttc attgagctta ttggagcgtt      660
ctgcggatgc cacggaacat cgagccaaat cccaggaaca cgctctgaac cccaggagct      720
gcacaccact ctattag                                                   737

<210> SEQ ID NO 9
<211> LENGTH: 210
<212> TYPE: DNA
<213> ORGANISM: Mus musculus

<400> SEQUENCE: 9
agcctcgaga attcatgctg ctctgggtgc tctttgtgat cctcatcctc accagtggct       60
cccactgctc atcactgccc ccctcacctc ccttcaggat tcagcgacag gaagacagca      120
tgtggacaga ggacaagcag atgaccctgg agagcatctt gcaggattcc ccaaggatga      180
agccttcagc ggacgcttga gtcgacccgg                                      210

<210> SEQ ID NO 10
<211> LENGTH: 30
<212> TYPE: DNA
<213> ORGANISM: Rattus norvegicus

<400> SEQUENCE: 10
ggctgttcat gatttcgtgc agcagtttgc                                       30

<210> SEQ ID NO 11
```

```
<211> LENGTH: 27
<212> TYPE: DNA
<213> ORGANISM: Rattus norvegicus

<400> SEQUENCE: 11
atataattgg cccaggattc tccggta                                    27

<210> SEQ ID NO 12
<211> LENGTH: 24
<212> TYPE: DNA
<213> ORGANISM: Rattus norvegicus

<400> SEQUENCE: 12
catgcagacg ccatcttcac cagc                                       24

<210> SEQ ID NO 13
<211> LENGTH: 22
<212> TYPE: DNA
<213> ORGANISM: Rattus norvegicus

<400> SEQUENCE: 13
acggaacatc gagccaaatc ca                                         22

<210> SEQ ID NO 14
<211> LENGTH: 20
<212> TYPE: DNA
<213> ORGANISM: Rattus norvegicus

<400> SEQUENCE: 14
ctggatccca caactgcaca                                            20

<210> SEQ ID NO 15
<211> LENGTH: 21
<212> TYPE: DNA
<213> ORGANISM: Rattus norvegicus

<400> SEQUENCE: 15
agagggatac ctgtcacctc a                                          21

<210> SEQ ID NO 16
<211> LENGTH: 20
<212> TYPE: DNA
<213> ORGANISM: Rattus norvegicus

<400> SEQUENCE: 16
tgcccccctc acctcccctc                                            20

<210> SEQ ID NO 17
<211> LENGTH: 20
<212> TYPE: DNA
<213> ORGANISM: Rattus norvegicus

<400> SEQUENCE: 17
ggcggttgaa cctggatctt                                            20

<210> SEQ ID NO 18
<211> LENGTH: 21
<212> TYPE: DNA
<213> ORGANISM: Rattus norvegicus

<400> SEQUENCE: 18
cattgagctt attggagcgt t                                          21
```

```
<210> SEQ ID NO 19
<211> LENGTH: 28
<212> TYPE: DNA
<213> ORGANISM: Mus musculus

<400> SEQUENCE: 19
agacgaattc atgctgctct gggtgctc                                        28

<210> SEQ ID NO 20
<211> LENGTH: 36
<212> TYPE: DNA
<213> ORGANISM: Mus musculus

<400> SEQUENCE: 20
gggaagtcct acgtcgctgt ccttctgtcg tacacc                               36

<210> SEQ ID NO 21
<211> LENGTH: 36
<212> TYPE: DNA
<213> ORGANISM: Mus musculus

<400> SEQUENCE: 21
cccttcagga tgcagcgaca ggaagacagc atgtgg                               36

<210> SEQ ID NO 22
<211> LENGTH: 31
<212> TYPE: DNA
<213> ORGANISM: Mus musculus

<400> SEQUENCE: 22
ttcggaagtc gcctgccaac tcagctgcag a                                    31

<210> SEQ ID NO 23
<211> LENGTH: 60
<212> TYPE: PRT
<213> ORGANISM: Mus musculus

<400> SEQUENCE: 23

Met Leu Leu Trp Val Leu Phe Val Ile Leu Ile Leu Thr Ser Gly Ser
 1               5                  10                  15

His Cys Ser Leu Pro Pro Ser Pro Pro Phe Arg Met Gln Arg Gln Glu
            20                  25                  30

Asp Ser Met Trp Thr Glu Asp Lys Trp Met Thr Leu Glu Ser Ile Leu
        35                  40                  45

Gln Gly Phe Pro Arg Met Lys Pro Ser Ala Asp Ala
    50                  55                  60
```